United States Patent
Fusaka

(10) Patent No.: US 8,507,410 B2
(45) Date of Patent: *Aug. 13, 2013

(54) PYRIDAZINONE COMPOUND AND USE THEREOF

(75) Inventor: Takafumi Fusaka, Kobe (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 49 days.

This patent is subject to a terminal disclaimer.

(21) Appl. No.: 13/255,993

(22) PCT Filed: Mar. 12, 2010

(86) PCT No.: PCT/JP2010/054725
§ 371 (c)(1),
(2), (4) Date: Sep. 12, 2011

(87) PCT Pub. No.: WO2010/104217
PCT Pub. Date: Sep. 16, 2010

(65) Prior Publication Data
US 2012/0028803 A1    Feb. 2, 2012

(30) Foreign Application Priority Data
Mar. 13, 2009    (JP) .................................. 2009-060943

(51) Int. Cl.
*C07D 237/16*    (2006.01)
*A01N 43/58*    (2006.01)

(52) U.S. Cl.
USPC ........................................ 504/238; 544/240

(58) Field of Classification Search
USPC .................... 544/238, 239, 240; 514/252.01, 514/247; 504/238
See application file for complete search history.

(56) References Cited

U.S. PATENT DOCUMENTS
2009/0111696 A1    4/2009    Kiji et al.

FOREIGN PATENT DOCUMENTS
CA    2 474 239    7/2003
WO    2007/119434    10/2007

OTHER PUBLICATIONS

Washington State, Dept of Transport., 2006.*
Vincent, et al., Mycologia, 80(5), 1988, 673-678.*
Polumbo, Review of New Insecticides, 2001, U. Of Arizona.*
EFSA Scientific Report (2007), 108, 1-82.*
International Preliminary Report on Patentability issued Sep. 13, 2011 in International (PCT) Application No. PCT/JP2010/054725, of which the present application is the national stage.
International Search Report issued May 18, 2010 in International (PCT) Application No. PCT/JP2010/054725.
Columbian Office Action issued Feb. 12, 2013 in corresponding Columbian Patent Application No. 11-116710, with English language letter.
Canadian Office Action issued Mar. 25, 2013 in corresponding Canadian Application No. 2,645,272.

* cited by examiner

*Primary Examiner* — Susanna Moore
*Assistant Examiner* — Cecilia M Jaisle
(74) *Attorney, Agent, or Firm* — Wenderoth, Lind & Ponack, L.L.P.

(57) ABSTRACT

A pyridazinone compound represented by formula (I) wherein $R^1$ represents a $C_{1-6}$ alkyl group or a ($C_{1-6}$ alkyloxy) $C_{1-6}$ alkyl group, $R^2$ and $R^3$ represent hydrogen or a $C_{1-6}$ alkyl group, W represents halogen, etc., $Z^1$ represents a $C_{1-6}$ alkyl group, $Z^2$ represents a $C_{1-6}$ alkyl group, a $C_{3-8}$ cycloalkyl group, etc., and n represents 0, 1, 2, 3 or 4, has a weed-controlling effect and an arthropod-controlling effect.

(I)

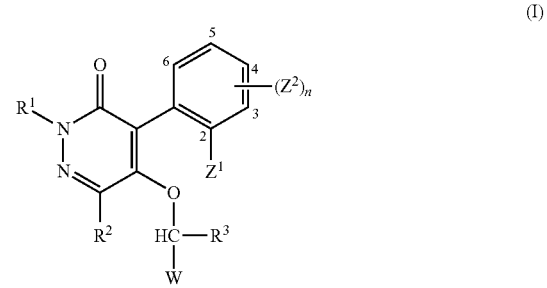

16 Claims, No Drawings

PYRIDAZINONE COMPOUND AND USE THEREOF

TECHNICAL FIELD

The present invention relates to a pyridazinone compound and use thereof.

BACKGROUND ART

A pyridazinone compound having herbicidal activity is disclosed in WO 2007/119434.

An object of the present invention is to provide a compound having excellent controlling effect against weeds and arthropods.

The resent invention provides the following.

[1] A pyridazinone compound represented by formula (I):

$$\text{(I)}$$

wherein $R^1$ represents a $C_{1-6}$ alkyl group or a $(C_{1-6}$ alkyloxy) $C_{1-6}$ alkyl group, $R^2$ and $R^3$ are the same or different, and represent hydrogen or a $C_{1-6}$ alkyl group, W represents halogen, or any one of the groups represented by the following formulas:

—$OR^4$, —$S(O)_mR^5$, —$OCOR^6$, —$NCOR^8$,
                                                    |
                                                   $R^7$

—$NCOR^9$, —$NSO_2R^{12}$
   |              |
  $COR^{10}$      $R^{11}$ wherein $R^4$, $R^5$, $R^7$ and $R^{11}$ each represent a $C_{1-6}$ alkyl group, a $C_{3-8}$ cycloalkyl group, a $C_{3-6}$ alkenyl group, a $C_{3-6}$ alkynyl group, a $C_{6-10}$ aryl group or a $(C_{6-10}$ aryl)$C_{1-6}$ alkyl group, $R^{12}$ represents a $C_{1-6}$ alkyl group, a $C_{3-8}$ cycloalkyl group, a $C_{3-6}$ alkenyl group, a $C_{3-6}$ alkynyl group, a $C_{6-10}$ aryl group or a $(C_{6-10}$ aryl)$C_{1-6}$ alkyl group, $R^6$, $R^8$ and $R^9$ each represent a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a $(C_{6-10}$ aryl)$C_{1-6}$ alkyl group, a $C_{1-6}$ alkyloxy group, a $C_{3-8}$ cycloalkyloxy group, a $C_{3-6}$ alkenyloxy group, a $C_{3-6}$ alkynyloxy group, a $C_{6-10}$ aryloxy group or a $(C_{6-10}$ aryl)$C_{1-6}$ alkyloxy group, $R^{10}$ represents a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a $(C_{6-10}$ aryl)$C_{1-6}$ alkyl group, a $C_{1-6}$ alkyloxy group, a $C_{3-8}$ cycloalkyloxy group, a $C_{3-6}$ alkenyloxy group, a $C_{3-6}$ alkynyloxy group, a $C_{6-10}$ aryloxy group or a $(C_{6-10}$ aryl)$C_{1-6}$ alkyloxy group, or $R^9$ and $R^{10}$ may represent, together with the carbonyl groups which they are attached and the nitrogen atom to which the carbonyl groups are attached, a 5- or 6-membered cyclic imide group to which a benzene ring may be fused, wherein, any group represented by $R^4$, $R^5$, $R^6$, $R^7$, $R^8$, $R^9$, $R^{10}$, $R^{11}$ or $R^{12}$ may be substituted with at least one member selected from the group consisting of halogen and $C_{1-6}$ alkyloxy groups, the $C_{3-8}$ cycloalkyl groups, the $C_{6-10}$ aryl groups, and the aryl moieties of the $(C_{6-10}$ aryl)$C_{1-6}$ alkyl groups which are represented by $R^4$, $R^5$, $R^6$, $R^7$, $R^8$, $R^9$, $R^{10}$, $R^{11}$ and $R^{12}$ may be substituted with at least one $C_{1-6}$ alkyl group, the $C_{3-8}$ cycloalkyloxy groups, the $C_{6-10}$ aryloxy groups, and the aryl moieties of the $(C_{6-10}$ aryl)$C_{1-6}$ alkyloxy groups which are represented by $R^6$, $R^8$, $R^9$ or $R^{10}$ may be substituted with at least one $C_{1-6}$ alkyl group, and m represents 0, 1 or 2, $Z^1$ represents a $C_{1-6}$ alkyl group, $Z^2$ represents a $C_{1-6}$ alkyl group, a $C_{3-8}$ cycloalkyl group, a $C_{2-6}$ alkynyl group, a $C_{1-6}$ haloalkyl group, a $C_{6-10}$ aryl group, a 5- or 6-membered heteroaryl group, a $C_{1-6}$ alkyloxy group, a $C_{1-6}$ haloalkyloxy group, halogen, a cyano group or a nitro group, wherein, the $C_{3-8}$ cycloalkyl group, the $C_{6-10}$ aryl group and the 5- or 6-membered heteroaryl group represented by $Z^2$ may be substituted with at least one member selected from the group consisting of halogen and $C_{1-6}$ alkyl groups, and n represents 0, 1, 2, 3 or 4, and when n is 2, 3 or 4, each $Z^2$ is the same or different.

[2] The pyridazinone compound according to [1], wherein n is 1, 2 or 3.

[3] The pyridazinone compound according to [1], wherein n is 0, and $Z^1$ is a $C_{2-6}$ alkyl group.

[4] The pyridazinone compound according to [1] or [2], wherein n is 1 or 2, and $Z^2$ is attached to the 4- and/or 6-position of the benzene ring.

[5] The pyridazinone compound according to [1], [2] or [4], wherein $Z^1$ is a $C_{1-3}$ alkyl group, $Z^2$ is a $C_{1-3}$ alkyl group, a $C_{3-6}$ cycloalkyl group, a $C_{2-3}$ alkynyl group, a $C_{1-3}$ alkyloxy group, halogen, a cyano group, a nitro group, or a phenyl group which may be substituted with at least one member selected from the group consisting of halogen and $C_{1-3}$ alkyl groups.

[6] The pyridazinone compound according to [1], [2], [4] or [5], wherein $Z^1$ is a $C_{1-3}$ alkyl group, and $Z^2$ is a $C_{1-3}$ alkyl group.

[7] The pyridazinone compound according to any one of [1] to [6], wherein $R^1$ is a $C_{1-3}$ alkyl group or a $(C_{1-3}$ alkyloxy) $C_{1-3}$ alkyl group.

[8] The pyridazinone compound according to any one of [1] to [6], wherein $R^1$ is a methyl group.

[9] The pyridazinone compound according to any one of [1] to [8], wherein $R^2$ is hydrogen or a $C_{1-3}$ alkyl group.

[10] The pyridazinone compound according to any one of [1] to [8], wherein $R^2$ is hydrogen or a methyl group.

[11] The pyridazinone compound according to any one of [1] to [10], wherein $R^3$ is hydrogen.

[12] The pyridazinone compound according to any one of [1] to [11], wherein W is halogen, a $C_{1-3}$ alkyloxy group, a $(C_{6-10}$ aryl)$C_{1-3}$ alkyloxy group, a $C_{1-3}$ alkylthio group, a $C_{1-3}$ alkylsulfinyl group, a $C_{1-3}$ alkylsulfonyl group or an N—$(C_{6-10}$ aryl)-N—$(C_{1-3}$ alkyloxycarbonyl)amino group.

[13] The pyridazinone compound according to any one of [1] to [11], wherein W is a $C_{1-3}$ alkyloxy group or a $C_{1-3}$ alkylthio group.

[14] A herbicidal composition comprising the pyridazinone compound according to any one of [1] to [13] and an inert carrier.

[15] A method of controlling weeds, which comprises applying an effective amount of the pyridazinone compound according to any one of [1] to [13] to weeds or soil where weeds grow.

[16] Use of the pyridazinone compound according to any one of [1] to [13] for the control of weeds.

[17] A method of controlling arthropods, which comprises applying an effective amount of the pyridazinone compound according to any one of [1] to [13] to arthropods or habitats of arthropods.

[18] Use of the pyridazinone compound according to any one of [1] to [13] for the control of arthropods.

MODE FOR CARRYING OUT THE INVENTION

As used herein, the $C_{1-6}$ alkyl group means an alkyl group having 1 to 6 carbon atoms. Examples of the $C_{1-6}$ alkyl group include a methyl group, an ethyl group, a propyl group, an isopropyl group, a butyl group, an isobutyl group, a sec-butyl group, a tert-butyl group, a pentyl group, a sec-pentyl group, an isopentyl group, a neopentyl group, a hexyl group and an isohexyl group.

As used herein, the $C_{3-8}$ cycloalkyl group means a cycloalkyl group having 3 to 8 carbon atoms. Examples of the $C_{3-8}$ cycloalkyl group include a cyclopropyl group, a cyclopentyl group and a cyclohexyl group.

As used herein, the $C_{2-6}$ alkenyl group means an alkenyl group having 2 to 6 carbon atoms. Examples of the $C_{2-6}$ alkenyl group include a vinyl group, an allyl group, a 1-buten-3-yl group and a 3-buten-1-yl group.

As used herein, the $C_{3-6}$ alkenyl group means an alkenyl group having 3 to 6 carbon atoms. Examples of the $C_{3-6}$ alkenyl group include an allyl group, a 1-buten-3-yl group and a 3-buten-1-yl group.

As used herein, the $C_{2-6}$ alkynyl group means an alkynyl group having 2 to 6 carbon atoms. Examples of the $C_{2-6}$ alkynyl group include an ethynyl group, a propargyl group and a 2-butynyl group.

As used herein, the $C_{3-6}$ alkynyl group means an alkynyl group having 3 to 6 carbon atoms. Examples of the $C_{3-6}$ alkynyl group include a propargyl group and a 2-butynyl group.

As used herein, the $C_{6-10}$ aryl group means an aryl group having 6 to 10 carbon atoms. Examples of the $C_{6-10}$ aryl group include a phenyl group and a naphthyl group.

As used herein, the $(C_{6-10}$ aryl$)C_{1-6}$ alkyl group means a $C_{1-6}$ alkyl group substituted with a $C_{6-10}$ aryl group. Examples of the $(C_{6-10}$ aryl$)C_{1-6}$ alkyl group includes a benzyl group and a phenethyl group.

As used herein, the $C_{1-6}$ alkyloxy group means an alkyloxy group having 1 to 6 carbon atoms. Examples of the $C_{1-6}$ alkyloxy group include a methoxy group, an ethoxy group, a propoxy group and an isopropoxy group.

As used herein, the $C_{3-8}$ cycloalkyloxy group means a cycloalkyloxy group having 3 to 8 carbon atoms. Examples of the $C_{3-8}$ cycloalkyloxy group include a cyclopropyloxy group and a cyclopentyloxy group.

As used herein, the $C_{3-6}$ alkenyloxy group means an alkenyloxy group having 3 to 6 carbon atoms. Examples of the $C_{3-6}$ alkenyloxy group include an allyloxy group.

As used herein, the $C_{3-6}$ alkynyloxy group means an alkynyloxy group having 3 to 6 carbon atoms. Examples of the $C_{3-6}$ alkynyloxy group include a propargyloxy group and a 2-butynyloxy group.

As used herein, the $C_{6-10}$ aryloxy group means an aryloxy group having 6 to 10 carbon atoms. Examples of the $C_{6-10}$ aryloxy group include a phenoxy group and a naphthyloxy group.

As used herein, the $(C_{6-10}$ aryl$)C_{1-6}$ alkyloxy group means a $C_{1-6}$ alkyloxy group substituted with a $C_{6-10}$ aryl group. Examples of the $(C_{6-10}$ aryl$)C_{1-6}$ alkyloxy group include a benzyloxy group and a phenethyloxy group.

As used herein, the $(C_{1-6}$ alkyloxy$)C_{1-6}$ alkyl group means a $C_{1-6}$ alkyl group substituted with a $C_{1-6}$ alkyloxy group. Examples of the $(C_{1-6}$ alkyloxy$)C_{1-6}$ alkyl group include a methoxyethyl group and an ethoxyethyl group.

Examples of the halogen include fluorine, chlorine, bromine and iodine.

Examples of the $C_{1-3}$ alkyloxy group include a methoxy group, an ethoxy group, a propoxy group and an isopropoxy group.

Examples of the $(C_{6-10}$ aryl$)C_{1-3}$ alkyloxy group include a benzyloxy group and a phenethyloxy group.

Examples of the $C_{1-3}$ alkylthio group include a methylthio group, an ethylthio group, a propylthio group and an isopropylthio group.

Examples of the $C_{1-3}$ alkylsulfinyl group include a methylsulfinyl group, an ethylsulfinyl group, a propylsulfinyl group and an isopropylsulfinyl group.

Examples of the $C_{1-3}$ alkylsulfonyl group include a methylsulfonyl group, an ethylsulfonyl group, a propylsulfonyl group and an isopropylsulfonyl group.

Examples of the N—($C_{6-10}$ aryl)-N—($C_{1-3}$ alkyloxycarbonyl)amino group include an N-ethoxycarbonyl-N-phenylamino group and an N-methoxycarbonyl-N-phenylamino group.

Examples of the 5- or 6-membered cyclic imide group to which a benzene ring may be fused, which is represented by $R^9$ and $R^{10}$ together with the carbonyl groups to which they are attached and the nitrogen to which the carbonyl groups are attached, include a succinimide group, a glutarimide group, a maleimide group and a phthalimide group.

Examples of the 5- or 6-membered heteroaryl group represented by $Z^2$ include a 3-pyridyl group, a 3-thienyl group and a 1-pyrazolyl group.

The $C_{1-6}$ haloalkyl group represented by $Z^2$ means a $C_{1-6}$ alkyl group substituted with halogen. Examples of $C_{1-6}$ haloalkyl group include a trifluoromethyl group and a 2,2,2-trichloroethyl group.

The $C_{1-6}$ haloalkyloxy group represented by $Z^2$ means a $C_{1-6}$ alkyloxy group substituted with halogen. Examples of the $C_{1-6}$ haloalkyloxy group include a trifluoromethoxy group and a 2,2,2-trifluoroethoxy group.

The groups represented by $R^4$, $R^5$, $R^6$, $R^7$, $R^8$, $R^9$, $R^{10}$, $R^{11}$ or $R^{12}$ may be substituted with at least one member selected from the group consisting of halogen and $C_{1-6}$ alkyloxy groups.

The $C_{3-8}$ cycloalkyl groups, the $C_{6-10}$ aryl groups, and the aryl moieties of the $(C_{6-10}$ aryl$)C_{1-6}$ alkyl groups which are represented by $R^4$, $R^5$, $R^6$, $R^7$, $R^8$, $R^9$, $R^{10}$, $R^{11}$ and $R^{12}$ may be substituted with at least one $C_{1-6}$ alkyl group.

The $C_{3-8}$ cycloalkyloxy groups, the $C_{6-10}$ aryloxy groups, and the aryl moieties of the $(C_{6-10}$ aryl$)C_{1-6}$ alkyloxy groups which are represented by $R^6$, $R^8$, $R^9$, or $R^{10}$ may be substituted with at least one $C_{1-6}$ alkyl group.

The $C_{3-8}$ cycloalkyl group, the $C_{6-10}$ aryl group and the 5- or 6-membered heteroaryl group represented by $Z^2$ may be substituted with at least one member selected from the group consisting of halogen and $C_{1-6}$ alkyl groups.

Examples of the compound of the present invention include the following compounds.

A pyridazinone compound of formula (I), wherein n is 1, 2 or 3.

A pyridazinone compound of formula (I), wherein n is 0, and $Z^1$ is a $C_{2-6}$ alkyl group.

A pyridazinone compound of formula (I), wherein n is 1 or 2, and when n is 2, each $Z^2$ may be the same or different, and $Z^2$ is, attached to the 4- and/or 6-position of the benzene ring.

A pyridazinone compound of formula (I), wherein $R^3$ is hydrogen.

A pyridazinone compound of formula (I), wherein W is halogen, a $C_{1-3}$ alkyloxy group, a $(C_{6-10}$ aryl$)C_{1-3}$ alkyloxy group, a $C_{1-3}$ alkylthio group, a $C_{1-3}$ alkylsulfinyl group, a $C_{1-3}$ alkylsulfonyl group or an N—$(C_{6-10}$ aryl)-N—$(C_{1-3}$ alkyloxycarbonyl)amino group.

A pyridazinone compound of formula (I), wherein W is a $C_{1-3}$ alkyloxy group or a $C_{1-3}$ alkylthio group.

A pyridazinone compound of formula (I), wherein $R^1$ is a $C_{1-3}$ alkyl group or a $(C_{1-3}$ alkyloxy$)C_{1-3}$ alkyl group.

A pyridazinone compound of formula (I), wherein $R^1$ is a methyl group.

A pyridazinone compound of formula (I), wherein $R^2$ is hydrogen or a $C_{1-3}$ alkyl group.

A pyridazinone compound of formula (I), wherein $R^2$ is hydrogen or a methyl group.

A pyridazinone compound of formula (I), wherein $Z^1$ is a $C_{1-3}$ alkyl group, and $Z^2$ is a $C_{1-3}$ alkyl group.

A pyridazinone compound of formula (I), wherein $Z^1$ is a $C_{1-3}$ alkyl group, and $Z^2$ is a $C_{1-3}$ alkyl group, a $C_{3-6}$ cycloalkyl group, a $C_{2-3}$ alkynyl group, a $C_{1-3}$ alkyloxy group, a $C_{1-3}$ haloalkyl group, a $C_{1-3}$ haloalkyloxy group, halogen, a cyano group, a nitro group, or a phenyl group which may be substituted with at least one member selected from the group consisting of halogen and $C_{1-3}$ alkyl groups.

A pyridazinone compound of formula (I), wherein $R^1$ is a $C_{1-3}$ alkyl group or a $(C_{1-3}$ alkyloxy$)C_{1-3}$ alkyl group, and $R^2$ is hydrogen or a $C_{1-3}$ alkyl group.

A pyridazinone compound of formula (I), wherein $R^1$ is a $C_{1-3}$ alkyl group or a $(C_{1-3}$ alkyloxy$)C_{1-3}$ alkyl group, and $R^2$ is hydrogen or a methyl group.

A pyridazinone compound of formula (I), wherein $R^2$ is hydrogen or a $C_{1-3}$ alkyl group, $R^3$ is hydrogen, and W is a $C_{1-3}$ alkyloxy group or a $C_{1-3}$ alkylthio group.

A pyridazinone compound of formula (I), wherein $R^2$ is hydrogen or a methyl group, $R^3$ is hydrogen, and W is a $C_{1-3}$ alkyloxy group or a $C_{1-3}$ alkylthio group.

A pyridazinone compound of formula (I), wherein $R^1$ is a $C_{1-3}$ alkyl group or a $(C_{1-3}$ alkyloxy$)C_{1-3}$ alkyl group, $R^2$ is hydrogen or a $C_{1-3}$ alkyl group, $R^3$ is hydrogen, and W is a $C_{1-3}$ alkyloxy group or a $C_{1-3}$ alkylthio group.

A pyridazinone compound of formula (I), wherein $R^1$ is a $C_{1-3}$ alkyl group or a $(C_{1-3}$ alkyloxy$)C_{1-3}$ alkyl group, $R^2$ is hydrogen or a methyl group, $R^3$ is hydrogen, and W is a $C_{1-3}$ alkyloxy group or a $C_{1-3}$ alkylthio group.

A pyridazinone compound of formula (I), wherein $R^1$ is a $C_{1-3}$ alkyl group or a $(C_{1-3}$ alkyloxy$)C_{1-3}$ alkyl group, $R^2$ is hydrogen or a $C_{1-3}$ alkyl group,
n is 1 or 2, and when n is 2, each $Z^2$ may be the same or different, and $Z^2$ is attached to the 4- and/or 6-position of the benzene ring,
$Z^1$ is a $C_{1-6}$ alkyl group (for example, a $C_{1-3}$ alkyl group), and $Z^2$ is a $C_{1-6}$ alkyl group (for example, a $C_{1-3}$ alkyl group).

A pyridazinone compound of formula (I), wherein $R^1$ is a $C_{1-3}$ alkyl group or a $(C_{1-3}$ alkyloxy$)C_{1-3}$ alkyl group, $R^2$ is hydrogen or a $C_{1-3}$ alkyl group,
n is 1 or 2, and when n is 2, each $Z^2$ may be the same or different, and $Z^2$ is attached to the 4- and/or 6-position of the benzene ring,
$Z^1$ is a $C_{1-6}$ alkyl group (for example, a $C_{1-3}$ alkyl group), and $Z^2$ is a $C_{1-6}$ alkyl group (for example, a $C_{1-3}$ alkyl group), a $C_{3-8}$ cycloalkyl group (for example, a $C_{3-6}$ cycloalkyl group), a $C_{2-6}$ alkynyl group (for example, a $C_{2-3}$ alkynyl group), a $C_{1-6}$ alkyloxy group (for example, a $C_{1-3}$ alkyloxy group), a $C_{1-6}$ haloalkyl group (for example, a $C_{1-3}$ haloalkyl group), a $C_{1-6}$ haloalkyloxy group (for example, a $C_{1-3}$ haloalkyloxy group), halogen, a cyano group, a nitro group, or a $C_{6-10}$ aryl group (for example, a phenyl group) which may be substituted with at least one member selected from the group consisting of halogen and $C_{1-6}$ alkyl groups (for example, a $C_{1-3}$ alkyl group).

A pyridazinone compound of formula (I), wherein $R^1$ is a $C_{1-3}$ alkyl group or a $(C_{1-3}$ alkyloxy$)C_{1-3}$ alkyl group, $R^2$ is hydrogen or a $C_{1-3}$ alkyl group, $R^3$ is hydrogen, W is a $C_{1-3}$ alkyloxy group or a $C_{1-3}$ alkylthio group,
n is 1 or 2, and when n is 2, each $Z^2$ may be the same or different, and $Z^2$ is attached to the 4- and/or 6-position of the benzene ring,
$Z^1$ is a $C_{1-6}$ alkyl group (for example, a $C_{1-3}$ alkyl group), and $Z^2$ is a $C_{1-6}$ alkyl group (for example, a $C_{1-3}$ alkyl group).

A pyridazinone compound of formula (I), wherein $R^1$ is a $C_{1-3}$ alkyl group or a $(C_{1-3}$ alkyloxy$)C_{1-3}$ alkyl group, $R^2$ is hydrogen or a $C_{1-3}$ alkyl group, $R^3$ is hydrogen, W is a $C_{1-3}$ alkyloxy group or a $C_{1-3}$ alkylthio group,
n is 1 or 2, and when n is 2, each $Z^2$ may be the same or different, and $Z^2$ is attached to the 4- and/or 6-position of the benzene ring,
$Z^1$ is a $C_{1-6}$ alkyl group (for example, a $C_{1-3}$ alkyl group), and $Z^2$ is a $C_{1-6}$ alkyl group (for example, a $C_{1-3}$ alkyl group), a $C_{3-8}$ cycloalkyl group (for example, a $C_{3-6}$ cycloalkyl group), a $C_{2-6}$ alkynyl group (for example, a $C_{2-3}$ alkynyl group), a $C_{1-6}$ alkyloxy group (for example, a $C_{1-3}$ alkyloxy group), a $C_{1-6}$ haloalkyl group (for example, a $C_{1-3}$ haloalkyl group), a $C_{1-6}$ haloalkyloxy group (for example, a $C_{1-3}$ haloalkyloxy group), halogen, a cyano group, a nitro group, or a $C_{6-10}$ aryl group (for example, a phenyl group) which may be substituted with at least one member selected from the group consisting of halogen and $C_{1-6}$ alkyl groups (for example, a $C_{1-3}$ alkyl group).

A pyridazinone compound of formula (I), wherein $R^1$ is a $C_{1-3}$ alkyl group or a $(C_{1-3}$ alkyloxy$)C_{1-3}$ alkyl group, $R^2$ is hydrogen or a methyl group,
n is 1 or 2, and when n is 2, each $Z^2$ may be the same or different, and $Z^2$ is attached to the 4- and/or 6-position of the benzene ring,
$Z^1$ is a $C_{1-6}$ alkyl group (for example, a $C_{1-3}$ alkyl group), and $Z^2$ is a $C_{1-6}$ alkyl group (for example, a $C_{1-3}$ alkyl group).

A pyridazinone compound of formula (I), wherein $R^1$ is a $C_{1-3}$ alkyl group or a $(C_{1-3}$ alkyloxy$)C_{1-3}$ alkyl group, $R^2$ is hydrogen or a methyl group,
n is 1 or 2, and when n is 2, each $Z^2$ may be the same or different and represent, and $Z^2$ is attached to the 4- and/or 6-position of the benzene ring,
$Z^1$ is a $C_{1-6}$ alkyl group (for example, a $C_{1-3}$ alkyl group), and $Z^2$ is a $C_{1-6}$ alkyl group (for example, a $C_{1-3}$ alkyl group), a $C_{3-8}$ cycloalkyl group (for example, a $C_{3-6}$ cycloalkyl group), a $C_{2-6}$ alkynyl group (for example, a $C_{2-3}$ alkynyl group), a $C_{1-6}$ alkyloxy group (for example, a $C_{1-3}$ alkyloxy group), a $C_{1-6}$ haloalkyl group (for example, a $C_{1-3}$ haloalkyl group), a $C_{1-6}$ haloalkyloxy group (for example, a $C_{1-3}$ haloalkyloxy group), halogen, a cyano group, a nitro group, or a $C_{6-10}$ aryl group (for example, a phenyl group) which may be substituted with at least one member selected from the group consisting of halogen and $C_{1-6}$ alkyl groups (for example, a $C_{1-3}$ alkyl group).

A pyridazinone compound of formula (I), wherein $R^1$ is a $C_{1-3}$ alkyl group or a $(C_{1-3}$ alkyloxy$)C_{1-3}$ alkyl group, $R^2$ is hydrogen or a methyl group, $R^3$ is hydrogen, W is a $C_{1-3}$ alkyloxy group or a $C_{1-3}$ alkylthio group,
n is 1 or 2, and when n is 2, each $Z^2$ may be the same or different and represent, and $Z^2$ is attached to the 4- and/or 6-position of the benzene ring,
$Z^1$ is a $C_{1-6}$ alkyl group (for example, a $C_{1-3}$ alkyl group), and $Z^2$ is a $C_{1-6}$ alkyl group (for example, a $C_{1-3}$ alkyl group).

A pyridazinone compound of formula (I), wherein $R^1$ is a $C_{1-3}$ alkyl group or a $(C_{1-3}$ alkyloxy$)C_{1-3}$ alkyl group, is hydrogen or a methyl group, $R^3$ is hydrogen, W is a $C_{1-3}$ alkyloxy group or a $C_{1-3}$ alkylthio group,
n is 1 or 2, and when n is 2, each $Z^2$ may be the same or different and represent, and $Z^2$ is attached to the 4- and/or 6-position of the benzene ring,
$Z^1$ is a $C_{1-6}$ alkyl group (for example, a $C_{1-3}$ alkyl group), and $Z^2$ is a $C_{1-6}$ alkyl group (for example, a $C_{1-3}$ alkyl group), a $C_{3-8}$ cycloalkyl group (for example, a $C_{3-6}$ cycloalkyl group), a $C_{2-6}$ alkynyl group (for example, a $C_{2-3}$ alkynyl group), a $C_{1-6}$ alkyloxy group (for example, a $C_{1-3}$ alkyloxy group), a $C_{1-6}$ haloalkyl group (for example, a $C_{1-3}$ haloalkyl group), a $C_{1-6}$ haloalkyloxy group (for example, a $C_{1-3}$ haloalkyloxy group), halogen, a cyano group, a nitro group, or a $C_{6-10}$ aryl group (for example, a phenyl group) which may be substituted with at least one member selected from the group consisting of halogen and $C_{1-6}$ alkyl groups (for example, a $C_{1-3}$ alkyl group).

A pyridazinone compound of formula (I), wherein n is 1, and $Z^2$ is attached to the 5-position of the benzene ring;

A pyridazinone compound of formula (I), wherein $R^1$ is a $C_{1-3}$ alkyl group or a $(C_{1-3}$ alkyloxy$)C_{1-3}$ alkyl group, $R^2$ is hydrogen or a $C_{1-3}$ alkyl group,
n is 1, $Z^2$ is attached to the 5-position of the benzene ring,
$Z^1$ is a $C_{1-6}$ alkyl group (for example, a $C_{1-3}$ alkyl group), and $Z^2$ is a $C_{6-10}$ aryl group (for example, a phenyl group) which may be substituted with at least one member selected from the group consisting of halogen and $C_{1-6}$ alkyl groups (for example, a $C_{1-3}$ alkyl group).

A pyridazinone compound of formula (I), wherein $R^1$ is a $C_{1-3}$ alkyl group or a $(C_{1-3}$ alkyloxy$)C_{1-3}$ alkyl group, $R^2$ is hydrogen or a $C_{1-3}$ alkyl group, $R^3$ is hydrogen, W is a $C_{1-3}$ alkyloxy group or a $C_{1-3}$ alkylthio group,
n is 1, $Z^2$ is attached to the 5-position of the benzene ring,
$Z^1$ is a $C_{1-6}$ alkyl group (for example, a $C_{1-3}$ alkyl group), and $Z^2$ is a $C_{6-10}$ aryl group (for example, a phenyl group) which may be substituted with at least one member selected from the group consisting of halogens and $C_{1-6}$ alkyl groups (for example, a $C_{1-3}$ alkyl group).

A pyridazinone compound of formula (I), wherein $R^1$ is $C_{1-3}$ alkyl group or a $(C_{1-3}$ alkyloxy$)C_{1-3}$ alkyl group, $R^2$ is hydrogen or a methyl group,
n is 1, $Z^2$ is attached to the 5-position of the benzene ring,
$Z^1$ is a $C_{1-6}$ alkyl group (for example, a $C_{1-3}$ alkyl group), and $Z^2$ is a $C_{6-10}$ aryl group (for example, a phenyl group) which may be substituted with at least one member selected from the group consisting of halogen and $C_{1-6}$ alkyl groups (for example, a $C_{1-3}$ alkyl group).

A pyridazinone compound of formula (I), wherein $R^1$ is a $C_{1-3}$ alkyl group or a $(C_{1-3}$ alkyloxy$)C_{1-3}$ alkyl group, $R^2$ is hydrogen or a methyl group, $R^3$ is hydrogen, W is a $C_{1-3}$ alkyloxy group or a $C_{1-3}$ alkylthio group,
n is 1, $Z^2$ is attached to the 5-position of the benzene ring,
$Z^1$ is a $C_{1-6}$ alkyl group (for example, a $C_{1-3}$ alkyl group), and $Z^2$ is a $C_{6-10}$ aryl group (for example, a phenyl group) which may be substituted with at least one member selected from the group consisting of halogen and $C_{1-6}$ alkyl groups (for example, a $C_{1-3}$ alkyl group).

A pyridazinone compound of formula (I-A):

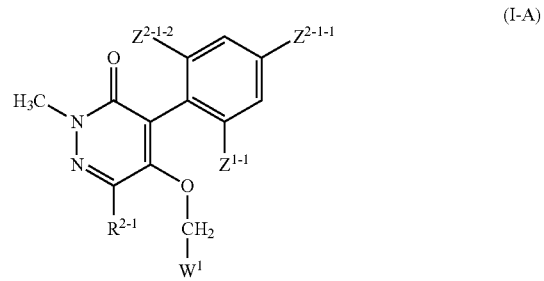

(I-A)

wherein
$R^{2-1}$ represents hydrogen or a $C_{1-3}$ alkyl group,
$W^1$ represents halogen, a $C_{1-3}$ alkyloxy group, a $(C_{6-10}$ aryl$)C_{1-3}$ alkyloxy group, a $C_{1-3}$ alkylthio group, a $C_{1-3}$ alkylsulfinyl group, a $C_{1-3}$ alkylsulfonyl group or an N—$(C_{6-10}$ aryl)-N—$(C_{1-3}$ alkyloxycarbonyl)amino group,
$Z^{1-1}$ represents a $C_{1-3}$ alkyl group,
$Z^{2-1-1}$ represents a $C_{1-3}$ alkyl group, and
$Z^{2-1-2}$ represents hydrogen or a $C_{1-3}$ alkyl group.

A pyridazinone compound of formula (I-A), wherein $R^{2-1}$ is hydrogen, a methyl group or an ethyl group, $W^1$ is chlorine, a methoxy group, an ethoxy group, a benzyloxy group, a methylthio group, a methylsulfinyl group, a methylsulfonyl group or an N-phenyl-N-ethoxycarbonylamino group,
$Z^{1-1}$ is a methyl group or an ethyl group,
$Z^{2-1-1}$ is a methyl group or an ethyl group, and
$Z^{2-1-2}$ is hydrogen, a methyl group or an ethyl group.

A pyridazinone compound of formula (I-A), wherein $R^{2-1}$ is hydrogen or a $C_{1-3}$ alkyl group, $W^1$ is halogen, a $C_{1-3}$ alkyloxy group, a $(C_{6-10}$ aryl$)C_{1-3}$ alkyloxy group, a $C_{1-3}$ alkylthio group, a $C_{1-3}$ alkylsulfinyl group, a $C_{1-3}$ alkylsulfonyl group or an N—$(C_{6-10}$ aryl)-N—$(C_{1-3}$ alkyloxycarbonyl) amino group,
$Z^{1-1}$ is a $C_{1-3}$ alkyl group,
$Z^{2-1-1}$ is a $C_{3-6}$ cycloalkyl group, a $C_{2-3}$ alkynyl group, a $C_{1-3}$ alkyloxy group, a $C_{1-3}$ haloalkyl group, a $C_{1-3}$ haloalkyloxy group, halogen, a cyano group, a nitro group, or a phenyl group which may be substituted with at least one member selected from the group consisting of halogen and $C_{1-3}$ alkyl groups, and
$Z^{2-1-2}$ is hydrogen, a $C_{1-3}$ alkyl group, a $C_{3-6}$ cycloalkyl group, a $C_{2-3}$ alkynyl group, a $C_{1-3}$ alkyloxy group or halogen.

A pyridazinone compound of formula (I-A), wherein $R^{2-1}$ is hydrogen, a methyl group or an ethyl group, $W^1$ is chlorine, a methoxy group, an ethoxy group, a benzyloxy group, a methylthio group, a methylsulfinyl group, a methylsulfonyl group or an N-phenyl-N-ethoxycarbonylamino group,
$Z^{1-1}$ is a methyl group or an ethyl group,
$Z^{2-1-1}$ is a cyclopropyl group, an ethynyl group, a methoxy group, a trifluoromethyl group, a trifluoromethoxy group, chlorine, bromine, a phenyl group, a 4-methylphenyl group, a cyano group or a nitro group, and
$Z^{2-1-2}$ is hydrogen, a methyl group, an ethyl group, a cyclopropyl group, an ethynyl group, a methoxy group, chlorine or bromine.

A pyridazinone compound of formula (I-A), wherein $R^{2-1}$ is hydrogen or a $C_{1-3}$ alkyl group, $W^1$ is halogen, a $C_{1-3}$ alkyloxy group, a $(C_{6-10}$ aryl$)C_{1-3}$ alkyloxy group, a $C_{1-3}$ alkylthio group, a $C_{1-3}$ alkylsulfinyl group, a $C_{1-3}$ alkylsulfonyl group or an N—($C_{6-10}$ aryl)-N—($C_{1-3}$ alkyloxycarbonyl)amino group, $Z^{1-1}$ is a $C_{1-3}$ alkyl group, $Z^{2-1-1}$ is hydrogen, a $C_{1-3}$ alkyl group, a $C_{3-6}$ cycloalkyl group, a $C_{2-3}$ alkynyl group, a $C_{1-3}$ alkyloxy group or halogen, and $Z^{2-1-2}$ is a $C_{3-6}$ cycloalkyl group, a $C_{2-3}$ alkynyl group, a $C_{1-3}$ alkyloxy group, halogen, a cyano group or a nitro group.

A pyridazinone compound of formula (I-A), wherein $R^{2-1}$ is hydrogen, a methyl group or an ethyl group, $W^1$ is chlorine, a methoxy group, an ethoxy group, a benzyloxy group, a methylthio group, a methylsulfinyl group, a methylsulfonyl group or an N-phenyl-N-ethoxycarbonylamino group, $Z^{1-1}$ is a methyl group or an ethyl group, $Z^{2-1-1}$ is hydrogen, a methyl group, an ethyl group, a cyclopropyl group, an ethynyl group, a methoxy group, chlorine or bromine, and $Z^{2-1-2}$ is a cyclopropyl group, an ethynyl group, a methoxy group, chlorine, bromine, a cyano group or a nitro group.

A pyridazinone compound of formula (I-B):

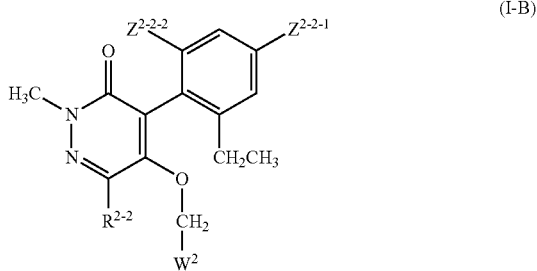

(I-B)

wherein $R^{2-2}$ represents hydrogen or a $C_{1-3}$ alkyl group, $W^2$ represents halogen, a $C_{1-3}$ alkyloxy group, a ($C_{6-10}$ aryl) $C_{1-3}$ alkyloxy group, a $C_{1-3}$ alkylthio group, a $C_{1-3}$ alkylsulfinyl group, a $C_{1-3}$ alkylsulfonyl group or an N—($C_{6-10}$ aryl)-N—($C_{1-3}$ alkyloxycarbonyl)amino group, $Z^{2-2-1}$ represents hydrogen or a $C_{1-3}$ alkyl group, and $Z^{2-2-2}$ represents hydrogen or a $C_{1-3}$ alkyl group.

A pyridazinone compound of formula (I-B), wherein $R^{2-2}$ is hydrogen, a methyl group or an ethyl group, $W^2$ is chlorine, a methoxy group, an ethoxy group, a benzyloxy group, a methylthio group, a methylsulfinyl group, a methylsulfonyl group or an N-phenyl-N-ethoxycarbonylamino group, $Z^{2-2-1}$ is hydrogen, a methyl group or an ethyl group, and $Z^{2-2-2}$ is hydrogen, a methyl group or an ethyl group.

A pyridazinone compound of formula (I-C):

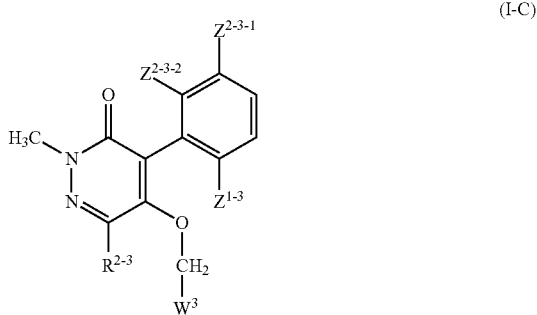

(I-C)

wherein $R^{2-3}$ represents hydrogen or a $C_{1-3}$ alkyl group, $W^3$ represents halogen, a $C_{1-3}$ alkyloxy group, a ($C_{6-10}$ aryl) $C_{1-3}$ alkyloxy group, a $C_{1-3}$ alkylthio group, a $C_{1-3}$ alkylsulfinyl group, a $C_{1-3}$ alkylsulfonyl group or an N—($C_{6-10}$ aryl)-N—($C_{1-3}$ alkyloxycarbonyl)amino group, $Z^{1-3}$ represents a $C_{1-3}$ alkyl group, $Z^{2-3-1}$ represents a phenyl group which may be substituted with at least one member selected from the group consisting of halogen and $C_{1-3}$ alkyl groups, and $Z^{2-3-2}$ represents hydrogen, a $C_{1-3}$ alkyl group or halogen.

A pyridazinone compound of formula (I-C), wherein $R^{2-3}$ is hydrogen, a methyl group or an ethyl group, $W^3$ is chlorine, a methoxy group, an ethoxy group, a benzyloxy group, a methylthio group, a methylsulfinyl group, a methylsulfonyl group or an N-phenyl-N-ethoxycarbonylamino group, $Z^{1-3}$ is a methyl group or an ethyl group, $Z^{2-3-1}$ is a phenyl group, a 4-fluorophenyl group or a 4-chlorophenyl group, and $Z^{2-3-2}$ is hydrogen, a methyl group or chlorine.

The herbicidal composition of the present invention and the arthropod controlling composition contain the compound of the present invention and an inert carrier. The inert carrier includes a solid carrier, a liquid carrier and a gas carrier. The herbicidal composition of the present invention and the arthropod controlling composition usually further contain an auxiliary agent for formulation, such as a surfactant, a binder, a dispersant or a stabilizer, and are formulated into a wettable powder, a water dispersible granule, a suspension concentrate, a granule, a dry flowable formulation, an emulsifiable concentrate, a liquid formulation, an oil solution, a smoking agent, an aerosol or a microcapsule. The herbicidal composition of the present invention and the arthropod controlling composition usually contain 0.1 to 80% by weight of the compound of the present invention.

Examples of the solid carrier include finely-divided powder and granules of clay [e.g., kaolin clay, diatomaceous earth, synthetic hydrated silicon oxide, agalmatolite clay (Fubasami clay), bentonite, or acid clay], talcs, and other inorganic minerals (e.g., sericite, quartz, sulfur powder, activated carbon, calcium carbonate, or hydrated silica).

Examples of the liquid carrier include water, alcohols (e.g. methanol, ethanol), ketones (e.g. acetone, methyl ethyl ketone), aromatic hydrocarbons (e.g. benzene, toluene, xylene, ethylbenzene, methylnaphthalene), aliphatic hydrocarbons (e.g. n-hexane, cyclohexane, kerosene), esters (e.g. ethyl acetate, butyl acetate), nitriles (e.g. acetonitrile, isobutyronitrile etc.), ethers (e.g. dioxane, diisopropyl ether), acid amides (e.g. N,N-dimethylformamide, dimethylacetamide), and halogenated hydrocarbons (e.g. dichloroethane, trichloroethylene, carbon tetrachloride).

Examples of the gas carrier include fluorocarbon, butane gas, liquefied petroleum gas (LPG), dimethyl ether, and carbon dioxide gas.

Examples of the surfactant include alkyl sulfate esters, alkyl sulfonate salts, alkylaryl sulfonate salts, alkyl aryl ethers and their polyoxyethylene derivatives, polyoxyethylene glycol ethers, polyhydric alcohol esters, and sugar alcohol derivatives.

Examples of the auxiliary agent for formulation include a binder and a dispersant, specifically include casein, gelatin, polysaccharides (e.g. starch, gum arabic, cellulose derivatives, alginic acid), lignin derivatives, bentonite, saccharides, synthetic water-soluble polymers (e.g. polyvinyl alcohol, polyvinyl pyrrolidone, polyacrylic acids), PAP (isopropyl acid phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, fatty acids, and fatty acid esters.

The method of controlling weeds of the present invention comprises the step of applying an effective amount of the compound of the present invention to weeds or soil where weeds grow. For the method of controlling weeds of the present invention, the herbicidal composition of the present invention is usually used. Examples of application method of the herbicidal composition of the present invention include foliage treatment of weeds with the herbicidal composition of the present invention, treatment of the surface of soil where weeds grow with the herbicidal composition of the present invention, or soil incorporation of the herbicidal composition of the present invention into the soil where weeds grow. In the method of controlling weeds of the present invention, the compound of the present invention is used in an amount of usually 1 to 5,000 g, preferably 10 to 1,000 g per 10,000 m$^2$ of an area where weed control is desired.

The method of controlling arthropods of the present invention comprises applying an effective amount of the compound of the present invention to arthropods or habitats of arthropods. For the method of controlling arthropods of the present invention, a formulation which contains the compound of the present invention is usually used.

When the compound of the present invention is used for controlling arthropods in agriculture and forestry, the application amount is usually 1 to 10,000 g/ha, preferably 10 to 1,000 g/ha of the compound of the present invention. In the method of controlling arthropods of the present invention, for example, a formulation which contains the compound of the present invention can be applied to plants to be protected from arthropods by spraying. Also, soil can be treated with to formulation which contains the compound of the present invention to control arthropods living in the soil.

When the compound of the present invention is used for the control of arthropods in public and environmental health area, the application amount is usually 0.001 to 10 mg/m$^3$ of the compound of the present invention for application to space, and 0.001 to 100 mg/m$^2$ of the compound of the present invention for application to a plane.

The herbicidal composition of the present invention or the arthropod controlling composition could be used, for example, in the place where the following plants are cultivated.

"Plants":

agricultural crops: maize, rice, wheat, barley, rye, oat, sorghum, cotton, soybean, peanut, buckwheat, sugar beet, rape, sunflower, sugarcane, tobacco and the like;

vegetables: solanaceous vegetables (for example, egg plant, tomato, green pepper, red pepper, potato and the like), cucurbitaceous vegetables (for example, cucumber, pumpkin, zucchini, watermelon, melon and the like), brassicaceous vegetables (for example, Japanese radish, turnip, horseradish, kohlrabi, Chinese cabbage, cabbage, leaf mustard, broccoli, cauliflower and the like), compositae vegetables (for example, burdock, garland chrysanthemum, artichoke, lettuce and the like), liliaceae vegetables (for example, leek, onion, garlic, asparagus and the like), umbelliferous vegetables (for example, carrot, parsley, celery, wild parsnip and the like), chenopodiaceous vegetables (for example, spinach, Swiss chard and the like), labiatae vegetables (for example, perilla, mint, basil and the like), strawberry, sweet potato, Japanese yam, taro, and the like;

fruits: pomaceous fruits (for example, apple, pear, Japanese pear, Chinese quince, quince and the like), stone fruits (for example, peach, plum, nectarine, Japanese plum, mahaleb cherry, apricot, prune and the like), citrus fruits (for example, tangerine, orange, lemon, lime, grapefruit and the like), nuts (for example, chestnut, walnut, hazel, almond, pistachio, cashew nut, *macadamia* nut and the like), berries (for example, blueberry, cranberry, blackberry, raspberry and the like), grape, persimmon, olive, loquat, banana, coffee, date palm, coconut palm, oil palm and the like;

trees other than fruit trees: tea plant, mulberry, flowering trees and shrubs (for example, azalea, *camellia*, hydrangea, *Camellia sasanqua*, Japanese star anise, Japanese flowering cherry, tulip tree, crape myrtle, fragrant orange-colored olive and the like), roadside trees (for example, ash plant, birch, American dogwood, eucalyptus, ginkgo, lilac, maple, willow oak, poplar, cercis, liquidambar, plane tree, zelkova, *thuja*, *Abies*, hemlock spruce, needle juniper, pine, spruce fir, yew, elm, horse chestnut, and the like), coral tree, podocarp, cedar, Japanese cypress, croton, Japanese spindle, Japanese *Photinia* and the like;

lawn: *Zoysia* (zoysiagrass, *Zoysia matrella* and the like), Bermuda grasses (bermudagrass and the like), bent grasses (*Agrostis alba*, creeping bent grass, hiland bent and the like), blueglasses (meadow grass, bird grass and the like), fescue (tall fescue, chewings fescue, creeping red fescue and the like), orchard grass, timothy grass and the like; and others: flowers (for example, rose, carnation, chrysanthemum, prairie gentian, gypsophila, gerbera, marigold, salvia, petunia, verbena, tulip, aster, gentian, lily, pansy, cyclamen, orchid, convallaria, lavender, stock, ornamental cabbage, primula, poinsettia, gladiolus, cattleya, daisy, cymbidium, begonia and the like), bio-fuel plants (*Jatropha*, safflower, camelina, switchgrass, *Miscanthus*, reed canary grass, giant reed, kenaf, cassava, willow, algae and the like), ornamental plants, and the like.

The above-described "plants" include plants having resistance to herbicides such as HPPD inhibitors (e.g. isoxaflutole), ALS inhibitors (e.g. imazethapyr and thifensulfuron-methyl), EPSP synthesizing enzyme inhibitors (e.g. glyphosate), glutamine synthesizing enzyme inhibitors (e.g. glufosinate), acetyl CoA carboxylase inhibitors (e.g. sethoxydim), PPO inhibitors (e.g. flumioxazin), bromoxynil, dicamba, and 2,4-D, which resistance is imparted by a classical breeding method or a genetic engineering technique.

Examples of the "plants" having herbicide resistance imparted by a classical breeding method include rapeseed, wheat, sunflower, rice and corn resistant to an imidazolinone-type ALS inhibitor such as imazethapyr, which are already on the market under the trade name of Clearfield (registered trade mark). Likewise, soybean having resistance to a sulfonylurea-type ALS inhibitor such as thifensulfuron-methyl imparted by a classical breeding method is already on the market under the trade name of STS soybean.

Likewise, SR corn is an example of a plant having resistance to an acetyl CoA carboxylase inhibitor, such as a trione oxime-type herbicide or an aryloxy phenoxypropionic acid-type herbicide, imparted by a classical breeding method.

For example, plants provided with resistance to acetyl CoA carboxylase inhibitors are described in Proc. Natl. Acad. Sci. USA, Vol. 87, pp. 7175-7179 (1990).

In addition, a mutant acetyl CoA carboxylase which provides resistance to an acetyl CoA carboxylase inhibitor is reported, for example, in Weed Science vol. 53, pp.: 728-746 (2005). A plant having resistance to an acetyl CoA carboxylase inhibitor can be produced by introducing a gene encoding the mutant acetyl CoA carboxylase into a plant by a genetic engineering technique or by introducing a mutation related to impartation of resistance into a gene encoding acetyl CoA carboxylase of a plant.

Examples of "plants" having resistance imparted by a classical breeding method also include plants resistant to nematodes and aphids. As an example of a gene which imparts resistance to aphids, RAG1 is known.

Further, nucleic acids for introduction of a base substitution mutation can be introduced into a plant cell by chimeraplasty technique (see, Gura T., Repairing the Genome's Spelling. Mistakes, Science vol. 285, p. 316-318 (1999)) to induce a site-directed amino acid mutation in a plant gene to be targeted by a herbicide, and thereby a herbicide-resistant plant can be produced.

Examples of the "plants" having resistance imparted by a genetic engineering technique include corn, soybean, cotton, rapeseed and sugar beet cultivars having resistance to glyphosate, which are already on the market under the trade name of RoundupReady (registered trademark), Agrisure (registered trademark) GT, or the like. Similarly, there are corn, soybean, cotton, and rapeseed cultivars having resistance to glufosinate imparted by a genetic engineering technique, which are already on the market under the trade name of LibertyLink (registered trademark) or the like. Similarly, cotton having resistance to bromoxynil imparted by a genetic engineering technique is already on the market under the trade name of BXN.

The above-described "plants" also include plants having an ability to produce an insecticidal toxin, for example a selective toxin originated from Bacillus, which ability is imparted by a genetic engineering technique.

Examples of insecticidal toxins produced in such genetically engineered plants include insecticidal proteins derived from Bacillus cereus and Bacillus popilliae; insecticidal proteins such as δ-endotoxins derived from Bacillus thuringiensis (e.g. Cry1Ab, Cry1Ac, Cry1F, Cry1Fa2, Cry2Ab, Cry3A, Cry3Bb1 and Cry9C), VIP 1, VIP 2, VIP 3 and VIP 3A; insecticidal proteins derived from nematodes; toxins produced by animals such as scorpion toxins, spider toxins, bee toxins and insect-specific nerve toxins; fungal toxins; plant lectin; agglutinin; protease inhibitors such as trypsin inhibitors, serine protease inhibitors, patatin, cystatin, and papain inhibitors; ribosome-inactivating proteins (RIP) such as ricin, corn-RIP, abrin, luffin, saporin, and bryodin; steroid metabolizing enzymes such as 3-hydroxysteroid oxidase, ecdysteroid-UDP-glucosyltransferase, and cholesterol oxidase; ecdysone inhibitors; HMG-CoA reductase; ion channel inhibitors such as sodium channel inhibitors and calcium channel inhibitors; juvenile hormone esterase; diuretic hormone receptors; stilbene synthase; bibenzyl synthase; chitinase; and glucanase.

The toxins produced in such genetically engineered plants also include hybrid toxins, partly deficient toxins and modified toxins of insecticidal proteins such as δ-endotoxin proteins (e.g., Cry1Ab, Cry1Ac, Cry1F, Cry1Fa2, Cry2Ab, Cry3A, Cry3Bb1 and Cry9C), VIP1, VIP2, VIP3, and VIP3A. The hybrid toxin is made by combining different domains of the insecticidal proteins by a genetic engineering technique. An example of the partly deficient toxin includes Cry1Ab in which a part of amino acids is deleted. An example of the modified toxin includes a toxin in which one or more of amino acids of a naturally occurring toxin are substituted.

Examples of the insecticidal toxin and the genetically engineered crop plant having the ability to produce the insecticidal toxin are described, for example, in EP-A-0 374 753, WO 93/07278, WO 95/34656, EP-A-0 427 529, EP-A-451878, or WO 03/052073.

The genetically engineered crop plant having the ability to produce the insecticidal toxin particularly has resistance to attack by coleopteran pests, dipteran pests and lepidopteran pests.

Genetically engineered plants which have one or more pest-resistance genes and thereby produce one or more toxins are also known, and some of them are commercially available. Examples of such genetically engineered plants include YieldGard (registered trademark) (a corn cultivar expressing Cry1Ab toxin), YieldGard Rootworm (registered trademark) (a corn cultivar expressing Cry3Bb1 toxin), YieldGard Plus (registered trademark) (a corn cultivar expressing Cry1Ab and Cry3Bb1 toxins), Herculex I (registered trademark) (a corn cultivar expressing Cry1Fa2 toxin and phosphinothricin N-acetyltransferase (PAT) for imparting resistance to glufosinate), NuCOTN33B (registered trademark) (a cotton cultivar expressing Cry1Ac toxin), Bollgard I (registered trademark) (a cotton cultivar expressing Cry1Ac toxin), Bollgard II (registered trademark) (a cotton cultivar expressing Cry1Ac and Cry2Ab toxins), VIPCOT (registered trademark) (a cotton cultivar expressing VIP toxin), NewLeaf (registered trademark) (a potato cultivar expressing Cry3A toxin), NatureGard Agrisure GT Advantage (registered trademark) (GA21 glyphosate-resistance character), Agrisure CB Advantage (registered trademark) (Bt11 corn borer (CB) character), and Protecta (registered trademark).

The above-described "plants" also include plants having an ability to produce an anti-pathogen substance which is imparted by a genetic engineering technique.

Examples of the anti-pathogen substance include PR proteins (PRPs, described in EP-A-0 392 225); ion channel inhibitors such as sodium channel inhibitors, and calcium channel inhibitors (e.g. KP1, KP4, and KP6 toxins produced by viruses); stilbene synthase; bibenzyl synthase; chitinase; glucanase; and substances produced by microorganisms such as peptide antibiotics, heterocycle-containing antibiotics, and protein factors involved in plant disease-resistance. Such anti-pathogen substances and genetically engineered plants which produce the anti-pathogen substances are described in EP-A-0 392 225, WO 95/33818, or EP-A-0 353 191.

The above-described "plants" include plants having beneficial traits such as a modified oil component and an enhanced amino acid content which are imparted by a genetic engineering technique. Examples of such plants include VISTIVE (registered trademark) (low linolenic soybean which has a reduced content of linolenic acid), and high-lysine (high-oil) corn (corn which has an increased content of lysine or oil).

Furthermore, the above-described "plants" include stacked plant varieties which have a combination of two or more of beneficial traits such as the above-described classical herbicide-resistant trait and herbicide-resistance gene, a pest-resistant insecticidal gene, an anti-pathogen substance-producing gene, a modified oil component, and an enhanced amino acid content.

When the compound of the present invention is used for a herbicide-resistant plant, the plant is treated sequentially with the compound of the present invention and the herbicide to which the plant is resistant (e.g., glyphosate or a salt thereof, glufosinate or a salt thereof, dicamba or a salt thereof, imazethapyr or a salt thereof, isoxaflutole), or with a mixture of both, and thereby comprehensive weed control can be attained.

The compound of the present invention can be used in admixture with or in combination with other insecticides, acaricides, nematocides, fungicides, herbicides, plant growth regulators, synergists and/or safeners.

Examples of active ingredients for the insecticides include:

(1) organophosphorous insecticidal compounds acephate, butathiofos, chlorethoxyfos, chlorfenvinphos, chlorpyrifos, chlorpyrifos-methyl, cyanophos: CYAP, diazinon, dichlofenthion: ECP, dichlorvos: DDVP, dimethoate, dimethylvinphos, disulfoton, EPN, ethion, ethoprophos, etrimfos, fenthion: MPP, fenitrothion: MEP, fosthiazate, formothion, isofenphos, isoxathion, malathion, mesulfenfos, methidathion: DMTP, monocrotophos, naled: BRP, oxydeprofos: ESP, parathion, phosalone, phosmet: PMP, pirimiphos-methyl, pyridafenthion, quinalphos, phenthoate: PAP, profenofos, propaphos, prothiofos, pyraclorfos, salithion, sulprofos, tebupirimfos, temephos, tetrachlorvinphos, terbufos, thiometon, trichlorphon: DEP, vamidothion, phorate, cadusafos;

(2) carbamate insecticidal compounds alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb: MIPC, metolcarb, methomyl, methiocarb, oxamyl, pirimicarb, propoxur: PHC, XMC, thiodicarb, xylylcarb, aldicarb;

(3) pyrethroid compounds acrinathrin, allethrin, beta-cyfluthrin, bifenthrin, cyclopro- thrin, cyfluthrin, cyhalothrin, cypermethrin, empenthrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, profluthrin, dimefluthrin, 2,3,5,6-tetrafluoro-4-(methoxymethyl)benzyl 2,2-dimethyl-3-(2-cyano-1-propenyl)cyclopropanecarboxylate, 2,3,5,6-tetrafluoro-4-(methoxymethyl)benzyl 2,2,3,3-tetramethylcyclopropanecarboxylate, protrifenbute;

(4) nereistoxin insecticidal compounds cartap, bensultap, thiocyclam, monosultap, bisultap;

(5) neonicotinoid compounds imidacloprid, nitenpyram, acetamiprid, thiamethoxam, thiacloprid, dinotefuran, clothianidin;

(6) benzoylurea insecticidal compounds chlorfluazuron, bistrifluoron, diflubenzuron, fluazuron, flucycloxuron, flufenoxuron, hexaflumuron, lufenuron, novaluron, noviflumuron, teflubenzuron, triflumuron;

(7) phenylpyrazole insecticidal compounds acetoprole, ethiprole, fipronil, vaniliprole, pyriprole, pyrafluprole;

(8) Bt toxin live spores or crystal toxins originated from *Bacillus thuringiensis* and a mixture thereof;

(9) hydrazine insecticidal compounds chromafenozide, halofenozide, methoxyfenozide, tebufenozide;

(10) organic chlorine insecticidal compounds aldrin, dieldrin, chlordane, DDT, dienochlor, endosulfan, methoxychlor; and

(11) other insecticidal active ingredients machine oil, nicotine-sulfate; avermectin-B, bromopropylate, buprofezin, chlorphenapyr, cyromazine, DCIP (dichlorodiisopropyl ether), D-D (1,3-Dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, Aluminum phosphide, Arsenous oxide, benclothiaz, Calcium cyanamide, Calcium polysulfide, DSP, flonicamid, flufenerim, formetanate, Hydrogen phosphide, metam-ammonium, metam-sodium, Methyl bromide, Potassium oleate, spiromesifen, Sulfur, metaflumizone, spirotetramat, pyrifluquinazone, spinetoram, chlorantraniliprole, tralopyril, diafenthiuron, a compound represented by formula (A):

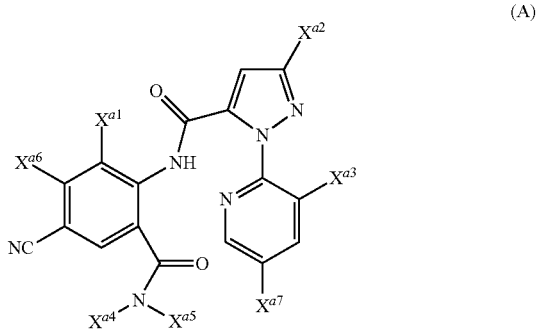

(A)

wherein $X^{a1}$ represents a methyl group, chlorine, bromine or fluorine, $X^{a2}$ represents fluorine, chlorine, bromine, a $C_1$-$C_4$ haloalkyl group or a $C_1$-$C_4$ haloalkoxy group, $X^{a3}$ represents fluorine, chlorine or bromine, $X^{a4}$ represents an optionally substituted $C_1$-$C_4$ alkyl group, an optionally substituted $C_3$-$C_4$ alkenyl group, an optionally substituted $C_3$-$C_4$ alkynyl group, an optionally substituted $C_3$-$C_5$ cycloalkylalkyl group or hydrogen, $X^{a5}$ represents hydrogen or a methyl group, $X^{a6}$ represents hydrogen, fluorine or chlorine, and $X^{a7}$ represents hydrogen, fluorine or chlorine, a compound represented by formula (B):

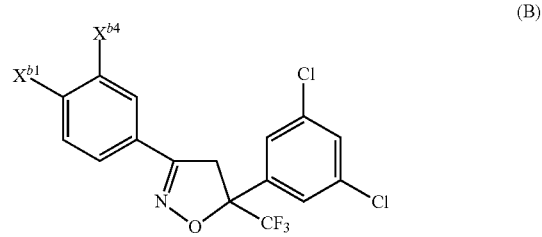

(B)

wherein $X^{b1}$ represents a $X^{b2}$—NH—C(=O) group, a $X^{b2}$—C(=O)—NH—CH$_2$ group, a $X^{b3}$—S(O) group, an optionally substituted pyrrol-1-yl group, an optionally substituted imidazol-1-yl group, an optionally substituted pyrazol-1-yl group or an optionally substituted 1,2,4-triazol-1-yl group, $X^{b2}$ represents an optionally substituted $C_1$-$C_4$ haloalkyl group such as a 2,2,2-trifluoroethyl group, or an optionally substituted $C_3$-$C_6$ cycloalkyl group such as a cyclopropyl group, $X^{b3}$ represents an optionally substituted $C_1$-$C_4$ alkyl group such as methyl group, and $X^{b4}$ represents hydrogen, chlorine, a cyano group or a methyl group;

a compound represented by formula (C):

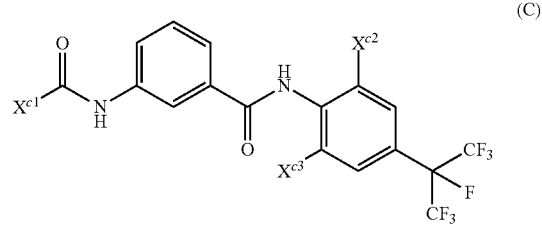

(C)

wherein $X^{c1}$ represents an optionally substituted $C_1$-$C_4$ alkyl group such as a 3,3,3-trifluoropropyl group, an optionally substituted $C_1$-$C_4$ alkoxy group such as a 2,2,2-trichloroethoxy group, an optionally substituted phenyl group such as a 4-cyanophenyl group, or an optionally substituted pyridyl group such as a 2-chloro-3-pyridyl group, $X^{c2}$ represents a methyl group or a trifluoromethylthio group, and $X^{c3}$ represents a methyl group or halogen.

Examples of active ingredients for the acaricides include: acequinocyl, amitraz, benzoximate, bifenazate, bromopropylate, chinomethionat, chlorobenzilate, CPCBS (chlorfenson), clofentezine, cyflumetofen, kelthane (dicofol), etoxazole, fenbutatin oxide, fenothiocarb, fenpyroximate, fluacrypyrim, halfenprox, hexythiazox, propargite: BPPS, polynactins, pyridaben, Pyrimidifen, tebufenpyrad, tetradifon, spirodiclofen, spiromesifen, spirotetramat, amidoflumet, and cyenopyrafen.

Examples of active ingredients for the nematocides include:
DCIP, fosthiazate, levamisol, methyl isothiocyanate, morantel tartrate, and imicyafos.

Examples of active ingredients for the fungicides include:
(1) polyhaloalkylthio fungicidal compounds [captan, folpet and the like];
(2) organophosphorous fungicidal compounds [IBP, EDDP, tolclofos-methyl and the like];
(3) benzimidazole fungicidal compounds [benomyl, carbendazim, thiophanate-methyl, thiabendazole and the like];
(4) carboxamide fungicidal compounds [carboxin, mepronil, flutolanil, thifluzamid, furametpyr, boscalid, penthiopyrad and the like];
(5) dicarboximide fungicidal compounds [procymidone, iprodione, vinclozolin and the like];
(6) acylalanine fungicidal compounds (metalaxyl and the like);
(7) azole fungicidal compounds [triadimefon, triadimenol, propiconazole, tebuconazole, cyproconazole, epoxiconazole, prothioconazole, ipconazole, triflumizole, prochloraz, penconazole, flusilazole, diniconazole, bromuconazole, difenoconazole, metconazole, tetraconazole, myclobutanil, fenbuconazole, hexaconazole, fluquinconazole, triticonazole, bitertanol, imazalil, flutriafol and the like];
(8) morpholine fungicidal compounds [dodemorph, tridemorph, fenpropimorph and the like];
(9) strobilurin compounds [azoxystrobin, kresoxim-methyl, metominostrobin, trifloxystrobin, picoxystrobin, pyraclostrobin, fluoxastrobin, dimoxystrobin and the like];
(10) antibiotics [validamycin A, blasticidin S, kasugamycin, polyoxin and the like];
(11) dithiocarbamate fungicidal compounds [mancozeb, maneb, thiuram and the like]; and
(12) other fungicidal active ingredients [fthalide, probenazole, isoprothiolane, tricyclazole, pyroquilon, ferimzone, acibenzolar S-methyl, carpropamid, diclocymet, fenoxanil, tiadinil, diclomezine, teclofthalam, pencycuron, oxolinic acid, TPN, triforine, fenpropidin, spiroxamine, fluazinam, iminoctadine, fenpiclonil, fludioxonil, quinoxyfen, fenhexamid, silthiofam, proquinazid, cyflufenamid, bordeaux mixture, dichlofluanid, cyprodinil, pyrimethanil, mepanipyrim, diethofencarb, pyribencarb, famoxadone, fenamidone, zoxamide, ethaboxam, amisulbrom, iprovalicarb, benthiavalicarb, cyazofamid, mandipropamid, metrafenone, fluopiram, bixafen and the like].

Examples of active ingredients for the herbicides include:
(1) phenoxy fatty acid herbicidal compounds [2,4-PA, MCP, MCPB, phenothiol, mecoprop, fluoroxypyr, triclopyr, clomeprop, naproanilide and the like];
(2) benzoate herbicidal compounds [2,3,6-TBA, dicamba, clopyralid, picloram, aminopyralid, quinclorac, quinmerac and the like];
(3) urea herbicidal compounds [diuron, linuron, chlortoluron, isoproturon, fluometuron, isouron, tebuthiuron, methabenzthiazuron, cumyluron, daimuron, methyl-daimuron and the like];
(4) triazine herbicidal compounds [atrazine, ametoryn, cyanazine, simazine, propazine, simetryn, dimethametryn, prometryn, metribuzin, triaziflam, indaziflam and the like];
(5) bipyridinium herbicidal compounds [paraquat, diquat and the like];
(6) hydroxybenzonitrile herbicidal compounds [bromoxynil, ioxynil and the like];
(7) dinitroaniline herbicidal compounds [pendimethalin, prodiamine, trifluralin and the like];
(8) organophosphorous herbicidal compounds [amiprofosmethyl, butamifos, bensulide, piperophos, anilofos, glyphosate, glufosinate, glufosinate-P, bialaphos and the like];
(9) carbamate herbicidal compounds [di-allate, tri-allate, EPTC, butylate, benthiocarb, esprocarb, molinate, dimepiperate, swep, chlorpropham, phenmedipham, phenisopham, pyributicarb, asulam and the like];
(10) acid amide herbicidal compounds [propanil, propyzamide, bromobutide, etobenzanid and the like];
(11) chloroacetanilide herbicidal compounds [acetochlor, alachlor, butachlor, dimethenamid, propachlor, metazachlor, metolachlor, pretilachlor, thenylchlor, pethoxamid and the like];
(12) diphenylether herbicidal compounds [acifluorfen-sodium, bifenox, oxyfluorfen, lactofen, fomesafen, chlomethoxynil, aclonifen and the like];
(13) cyclic imide herbicidal compounds [oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, benzfendizone, bencarbazone, saflufenacil and the like];
(14) pyrazole herbicidal compounds [benzofenap, pyrazolate, pyrazoxyfen, topramezone, pyrasulfotole and the like].
(15) triketone herbicidal compounds [isoxaflutole, benzobicyclon, sulcotrione, mesotrione, tembotrione, tefuryltrione, bicyclopyrone and the like];
(16) aryloxyphenoxypropionate herbicidal compounds [clodinafop-propargyl, cyhalofop-butyl, diclofop-methyl, fenoxaprop-ethyl, fluazifop-butyl, haloxyfop-methyl, quizalofop-ethyl, metamifop and the like];
(17) trioneoxime herbicidal compounds [alloxydim-sodium, sethoxydim, butroxydim, clethodim, cloproxydim, cycloxydim, tepraloxydim, tralkoxydim, profoxydim and the like];
(18) sulfonylurea herbicidal compounds [chlorsulfuron, sulfometuron-methyl, metsulfuron-methyl, chlorimuron-ethyl, tribenuron-methyl, triasulfuron, bensulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-methyl, trifloxysulfuron, tritosulfuron, orthosulfamuron, flucetosulfuron, propyrisulfuron, metazosulfuron and the like];
(19) imidazolinone herbicidal compounds [imazamethabenz-methyl, imazamethapyr, imazamox, imazapyr, imazaquin, imazethapyr and the like];

(20) sulfonamide herbicidal compounds [flumetsulam, metosulam, diclosulam, florasulam, cloransulam-methyl, penoxsulam, pyroxsulam and the like];

(21) pyrimidinyloxybenzoate herbicidal compounds [pyrithiobac-sodium, bispyribac-sodium, pyriminobac-methyl, pyribenzoxim, pyriftalid, pyrimisulfan and the like]; and

(22) other herbicidal active ingredients [bentazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, pyraclonil, pyroxasulfone, thiencarbazone-methyl, aminocyclopyrachlor, ipfencarbazone, methiozolin, fenoxasulfone and the like].

Examples of active ingredients for the plant growth regulators include:

hymexazol, paclobutrazol, uniconazole-P, inabenfide, prohexadione-calcium, aviglycine, 1-naphthaleneacetamide, abscisic acid, indolebutyric acid, ethychlozate, ethephon, cloxyfonac, chlormequat, dichlorprop, gibberellins, prohydrojasmon, benzyladenine, forchlorfenuron, maleic hydrazide, calcium peroxide, mepiquat-chloride, and 4-CPA (4-chlorophenoxyacetic acid).

Examples of active ingredients for the synergists include: piperonyl butoxide, sesamex, sulfoxide, N-(2-ethylhexyl)-8,9,10-trinorborn-5-ene-2,3-dicarboximide (MGK 264), N-decylimidazole, WARF-antiresistant, TBPT, TPP, IBP, PSCP, methyl iodide ($CH_3I$), t-phenylbutenone, diethyl maleate, DMC, FDMC, ETP, and ETN.

Examples of active ingredients for the safeners include: furilazole, dichlormid, benoxacor, allidochlor, isoxadifen-ethyl, fenchlorazole-ethyl, mefenpyr-diethyl, cloquintocet-mexyl, fenclorim, cyprosulfamide, cyometrinil, oxabetrinil, fluxofenim, flurazole, 2-dichloromethyl-2-methyl-1,3-dioxolane, and 1,8-naphthalic anhydride.

Examples of weeds which can be controlled by the compound of the present invention include:

*Digitaria ciliaris, Eleusine indica, Setaria viridis, Setaria faberi, Setaria glauca, Echinochloa crus-galli, Panicum dichotomiflorum, Panicum texanum, Brachiaria platyphylla, Brachiaria plantaginea, Sorghum halepense, Andropogon sorghum, Avena fatua, Lolium multiflorum, Alopecurus myosuroides, Bromus tectorum, Bromus sterilis, Phalaris minor, Apera spica-venti, Poa annua, Agropyron repens, Cyperus iria, Cyperus rotundus, Cyperus esculentus, Portulaca oleracea, Amaranthus retroflexus, Amaranthus hybridus, Abutilon theophrasti, Sida spinosa, Fallopia convolvulus, Polygonum scabrum, Persicaria pennsylvanica, Persicaria vulgaris, Rumex crispus, Rumex obtusifolius, Fallopia japonica, Chenopodium album, Kochia scoparia, Polygonum longisetum, Solanum nigrum, Datura stramonium, Ipomoea purpurea, Ipomoea hederacea, Ipomoea hederacea* var. *integriuscula, Ipomoea lacunosa, Convolvulus arvensis, Lamium purpureum, Lamium amplexicaule, Xanthium pensylvanicum, Helianthus annuus* (wild sunflower), *Matricaria perforata* or *inodora, Matricaria chamomilla, Chrysanthemum segetum, Matricaria matricarioides, Ambrosia artemisiifolia, Ambrosia trifida, Erigeron canadensis, Artemisia princeps, Solidago altissima, Conyza bonariensis, Sesbania exaltata, Cassia obtusifolia, Desmodium tortuosum, Trifolium repens, Pueraria lobata, Vicia angustifolia, Commelina communis, Commelina benghalensis, Galium aparine, Stellaria media, Raphanus raphanistrum, Sinapis arvensis, Capsella bursa-pastoris, Veronica persica, Veronica hederifolia, Viola arvensis, Viola tricolor, Papaver rhoeas, Myosotis scorpioides, Asclepias syriaca, Euphorbia helioscopia, Chamaesyce nutans, Geranium carolinianum, Erodium cicutarium, Equisetum arvense, Leersia japonica, Echinochloa oryzicola, Echinochloa crus-galli* var. *formosensis, Cyperus difformis, Fimbristylis miliacea, Eleocharis acicularis, Scirpus juncoides, Scirpus wallichii, Cyperus serotinus, Eleocharis kuroguwai, Bolboschoenus koshevnikovii, Schoenoplectus nipponicus, Monochoria vaginalis, Lindernia procumbens, Dopatrium junceum, Rotala indica, Ammannia multiflora, Elatine triandra, Ludwigia epilobioides, Sagittaria pygmaea, Alisma canaliculatum, Sagittaria trifolia, Potamogeton distinctus, Oenanthe javanica, Callitriche palustris, Lindernia micrantha, Lindernia dubia, Eclipta prostrata, Murdannia keisak, Paspalum distichum,* and *Leersia oryzoides.*

Examples of arthropods on which the compound of the present invention exhibits efficacy include harmful insects and harmful mites, and more specifically are included the following arthropods.

Hemiptera:

Planthoppers (Delphacidae) such as small brown planthopper (*Laodelphax striatellus*), brown rice planthopper (*Nilaparvata lugens*), and white-backed rice planthopper (*Sogatella furcifera*); leafhoppers (Deltocephalidae) such as green rice leafhopper (*Nephotettix cincticeps*), green rice leafhopper (*Nephotettix virescens*), and tea green leafhopper (*Empoasca onukii*); aphids (Aphididae) such as cotton aphid (*Aphis gossypii*), green peach aphid (*Myzus persicae*), cabbage aphid (*Brevicoryne brassicae*), spiraea aphid (*Aphis spiraecola*), potato aphid (*Macrosiphum euphorbiae*), foxglove aphid (*Aulacorthum solani*), oat bird-cherry aphid (*Rhopalosiphum padi*), tropical citrus aphid (*Toxoptera citricidus*), and mealy plum aphid (*Hyalopterus pruni*); stink bugs (Pentatomidae) such as green stink bug (*Nezara antennata*), bean bug (*Riptortus clavetus*), rice bug (*Leptocorisa chinensis*), white spotted spined bug (*Eysarcoris parvus*), and stink bug (*Halyomorpha mista*); whiteflies (Aleyrodidae) such as greenhouse whitefly (*Trialeurodes vaporariorum*), sweetpotato whitefly (*Bemisia tabaci*), silver leaf whitefly (*Bemisia argentifolii*), citrus whitefly (*Dialeurodes citri*), and citrus spiny whitefly (*Aleurocanthus spiniferus*); scales (Coccidae) such as Calformia red scale (*Aonidiella aurantii*), San Jose scale (*Comstockaspis perniciosa*), citrus north scale (*Unaspis citri*), red wax scale (*Ceroplastes rubens*), cottonycushion scale (*Icerya purchasi*), Japanese mealybug (*Planococcus kraunhiae*), Cosmstock mealybug (*Pseudococcus longispinus*), and white peach scale (*Pseudaulacaspis pentagona*); lace bugs (Tingidae); cimices such as *Cimex lectularius*; psyllids (Psyllidae);

Lepidoptera:

Pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogata*), Indian meal moth (*Plodia interpunctella*), *Ostrinia furnacalis*, cabbage webworm (*Hellula undalis*), and bluegrass webworm (*Pediasia teterrellus*); owlet moths (Noctuidae) such as common cutworm (*Spodoptera litura*), beet armyworm (*Spodoptera exigua*), armyworm (*Pseudaletia separata*), cabbage armyworm (*Mamestra brassicae*), black cutworm (*Agrotis ipsilon*), beet semi-looper (*Plusia nigrisigna*), *Thoricoplusia* spp., *Heliothis* spp., and *Helicoverpa* spp.; white butterflies (Pieridae) such as common white (*Pieris rapae*); tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit tortrix (*Adoxophyes orana* fasciata), smaller tea tortrix (*Adoxophyes* sp.), oriental tea tortrix (*Homona magnanima*), apple tortrix (*Archips fuscocupreanus*), and codling moth (*Cydia pomonella*); leafblotch miners (Gracillariidae) such as tea leafroller (*Caloptilia theivora*), and apple leafminer (*Phyllonorycter ringoneella*); Carposimidae such as peach fruit moth (*Carposina niponensis*); lyonetiid moths (Lyonetiidae) such as *Lyonetia* spp.; tussock moths (Lymantriidae) such as *Lymantria* spp., and *Euproctis* spp.; yponomeutid moths (Yponomeutidae) such as diamondback (*Plutella xylostella*); gelechiid moths (Gelechiidae) such as pink bollworm (*Pectinophora gossypiella*), and potato tubeworm (*Phthorimaea operculella*); tiger moths and allies (Arctiidae) such as fall webworm (*Hyphantria cunea*); tineid moths (Tineidae) such as casemaking clothes moth (*Tinea translucens*), and webbing clothes moth (*Tineola bisselliella*);

Thysanoptera:

Yellow citrus thrips (*Frankliniella occidentalis*), melon thrips (*Thrips palmi*), yellow tea thrips (*Scirtothrips dorsalis*), onion thrips (*Thrips tabaci*), flower thrips (*Frankliniella intonsa*);

Diptera:

House mosquitoes (*Culex* spp.) such as common mosquito (*Culex pipiens pallens*), *Culex tritaeniorhynchus*, and *Culex quinquefasciatus*; *Aedes* spp. such as yellow fever mosquito (*Aedes aegypti*) and Asian tiger mosquito (*Aedes albopictus*); *Anopheles* spp. such as *Anqpheles sinensis*; Chironomidae; house flies (Muscidae) such as housefly (*Musca domestica*) and false stable fly (*Muscina stabulans*); blowflies (Calliphoridae); fleshflies (Sarcophagidae); *Fannia canicularis*; Anthomyiidae such as seedcorn maggot (*Delia platura*) and onion maggot (*Delia antiqua*); leafminers (Agromyzidae) such as rice leafminer (*Agromyza oryzae*), rice leafminer (*Hydrellia griseola*), tomato leafminer (*Liriomyza sativae*), legume leafminer (*Liriomyza trifolii*), and garden pea leafminer (*Chromatomyia horticola*); gout flies (Chloropidae) such as rice stem maggot (*Chlorqps oryzae*); fruit flies (Tephritidae) such as melon fly (*Dacus cucurbitae*), and Mediteranean fruit fly (*Ceratitis capitata*); Drosophilidae; Phoridae such as *Megaselia spiracularis*; moth flies (Psychodidae) such as *Clogmia albipunctata*; Simuliidae; Tabanidae such as horsefly (*Tabanus trigonus*); stable flies (Stomoxyidae);

Coleoptera:

Corn root worms (*Diabrotica* spp.) such as Western corn root worm (*Diabrotica virgifera* virgifera), and Southern corn root worm (*Diabrotica undecimpunctata* howardi); scarabs (Scarabaeidae) such as cupreous chafer (*Anomala cuprea*), soybean beetle (*Anomala rufocuprea*), and Japanese beetle (*Popillia japonica*); weevils (Curculionidae) such as maize weevil (*Sitophilus zeamais*), rice water weevil (*Lissorhoptrus oryzophilus*), azuki bean weevil (*Callosobruchus chinensis*), rice curculio (*Echinocnemus squameus*), boll weevil (*Anthonomus grandis*), and hunting billbug (*Sphenophorus venatus*); darkling beetles (Tenebrionidae) such as yellow mealworm (*Tenebrio molitor*), and red flour beetle (*Tribolium castaneum*); leaf beetles (Chrysomelidae) such as rice leaf beetle (*Oulema oryzae*), cucurbit leaf beetle (*Aulacophora femoralis*), striped flea beetle (*Phyllotreta striolata*), and Colorado potato beetle (*Leptinotarsa decemlineata*); dermestid beetles (Dermestidae) such as varied carper beetle (*Anthrenus verbasci*), and hide beetle (*Dermestes maculates*); deathwatch beetles (Anobiidae) such as cigarette beetle (*Lasioderma serricorne*); *Epilachna* such as twenty-eight-spotted ladybird (*Epilachna vigintioctopunctata*); bark beetles (Scolytidae) such as powder post beetle (*Lyctus brunneus*), and pine shoot beetle (*Tomicus piniperda*); false powderpost beetles (Bostrichidae); spider beetles (Ptimidae); longhorn beetles (Cerambycidae) such as white-spotted longicorn beetle (*Anoplophora malasiaca*); click beetles (*Agriotes* spp.); *Paederus fuscipes*;

Orthoptera:

Asiatic locust (*Locusta migratoria*), African mole cricket (*Gryllotalpa africana*), rice grasshopper (*Oxya yezoensis*), rice grasshopper (*Oxya japonica*), Grylloidea;

Siphonaptera:

Cat flea (*Ctenocephalides felis*), dog flea (*Ctenocephalides canis*), human flea (*Pulex irritans*), oriental rat flea (*Xenopsylla cheopis*);

Anoplura:

Human body louse (*Pediculus humanus corporis*), crab louse (*Phthirus pubis*), short-nosed cattle louse (*Haematopinus eurysternus*), sheep louse (*Damalinia ovis*), hog louse (*Haematopinus suis*);

Hymenoptera:

Ants (Formicidae) such as *Monomorium pharaonis*, *Formica fusca japonica*, black house ant (*Ochetellus glaber*), *Pristomyrmex pungens*, *Pheidole noda*, leaf-cutting ant (*Acromyrmex* spp.), and fire ant (*Solenopsis* spp.); hornets (Vespidae); bethylid wasps (Betylidae); sawflies (Tenthredimidae) such as Cabbage sawfly (*Athalia rosae*), and *Athalia japonica*;

Blattodea:

Cockroaches (Blattariae) such as German cockroach (*Blattella germanica*), smokybrown cockroach (*Periplaneta fuliginosa*), American cockroach (*Periplaneta americana*), *Periplaneta brunnea*, and oriental cockroach (*Blatta orientalis*);

Isoptera:

Termites (Termitidae) such as Japanese subterranean termite (*Reticulitermes speratus*), Formosan subterranean termite (*Coptotermes formosanus*), western drywood termite (*Incisitermes minor*), Daikoku drywood termite (*Cryptotermes domesticus*), *Odontotermes formosanus*, *Neotermes koshunensis*, *Glyptotermes satsumensis*, *Glyptotermes nakajimai*, *Glyptotermes fuscus*, *Glyptotermes kodamai*, *Glyptotermes kushimensis*, Japanese dampwood termite (*Hodotermopsis japonica*), *Coptotermes guangzhoensis*, *Reticulitermes miyatakei*, *Reticulitermes flavipes amamianus*, *Reticulitermes* sp., *Nasutitermes takasagoensis*, *Pericapritermes nitobei*, *Sinocapritermes mushae*, *Reticulitermes flavipes*, *Reticulitermes hesperus*, *Reticulitermes virginicus*, *Reticulitermes tibialis*, *Heterotermes aureus* and *Zootermopsis nevadensis* and;

Acarina:

Spider mites (Tetranychidae) such as two-spotted spider mite (*Tetranychus urticae*), Kanzawa spider mite (*Tetranychus kanzawai*), citrus red mite (*Panonychus citri*), European red mite (*Panonychus ulmi*), and *Oligonychus* spp.; eriophyid mites (Eriophyidae) such as pink citrus rust mite (*Aculops pelekassi*), *Phyllocoptruta citri*, tomato rust mite (*Aculops lycopersici*), purple tea mite (*Calacarus carinatus*), pink tea rust mite (*Acaphylla theavagran*), *Eriophyes chibaensis*, and apple rust mite (*Aculus schlechtendali*); tarosonemid mites (Tarsonemidae) such as broad mite (*Polyphagotarsonemus latus*); false spider mites (Tenuipalpidae) such as *Brevipalpus phoenicis*; Tuckerellidae; ticks (Ixodidae) such as *Haemaphysalis longicornis*, *Haemaphysalis flava*, *Dermacentor taiwanicus*, American dog tick (*Dermacentor variabilis*), *Ixodes ovatus*, *Ixodes persulcatus*, black legged tick (*Ixodes scapularis*), lone star tick (*Amblyomma americanum*), *Boophilus microplus*, and *Rhipicephalus sanguineus*; Psoroptidae such as ear mite (*Otodectes cynotis*); itch mites (Sarcoptidae) such as *Sarcoptes scabiei*; folicle mites (Demodicidae) such as dog folicle mite (*Demodex canis*);

acarid mites (Acaridae) such as mold mite (*Tyrophagus putrescentiae*), and *Tyrophagus similis*; house dust mites (Pyroglyphidae) such as *Dermatophagoides farinae*, and *Dermatophagoides ptrenyssnus*; cheyletide mites (Cheyletidae) such as *Cheyletus eruditus, Cheyletus malaccensis*, and *Cheyletus moorei*; parasitoid mites (Dermanyssidae) such as tropical rat mite (*Ornithonyssus bacoti*), northern fowl mite (*Ornithonyssus sylviarum*), and poultry red mite (*Dermanyssus gallinae*); chiggers (Trombiculidae) such as *Leptotrombidium akamushi*; spiders (Araneae) such as Japanese foliage spider (*Chiracanthium japonicum*), redback spider (*Latrodectus hasseltii*);

Chilopoda: *Thereuonema hilgendorfi, Scolopendra subspinipes*;

Diplopoda: garden millipede (*Oxidus gracilis*), *Nedyopus tambanus*;

Isopoda: common pill bug (*Armadillidium vulgare*).

The compound of the present invention can also be used for the control of parasites.

The compound of the present invention can be produced, for example, by the following Production Processes.

Production Process 1

The compound represented by formula (I) can be produced by reacting a compound represented by formula (II) with a compound represented by formula (III).

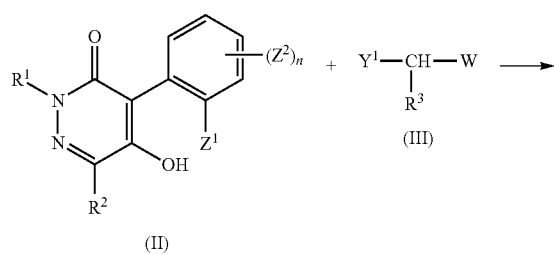

wherein $Y^1$ represents halogen or a group represented by the formula: $OSO_2R^{13}$ (wherein, $R^{13}$ represents a $C_{1-3}$ alkyl group or a phenyl group, in which the $C_{1-3}$ alkyl group may be substituted with halogen and the phenyl group may be substituted with halogen or $C_{1-3}$ alkyl group) and $R^1$, $R^2$, $R^3$, W, $Z^1$, $Z^2$ and n are as defined above.

The reaction is performed in a solvent. Examples of the solvent used in the reaction include aromatic hydrocarbons such as benzene, toluene and xylene; ethers such as diethylether, diisopropylether, dioxane, tetrahydrofuran and dimethoxyethane; halogenated hydrocarbons such as dichloromethane, chloroform and 1,2-dichloroethane; ketones such as acetone and methyl ethyl ketone; nitriles such as acetonitrile; esters such as ethyl acetate; amides such as dimethylformamide and dimethylacetamide; sulfoxides such as dimethyl sulfoxide; sulfones such as sulfolane; and mixtures thereof.

The amount of the compound of formula (III) used in the reaction is usually 1 mol or more, preferably 1 to 3 mol per 1 mol of the compound of formula (II).

The reaction is usually performed in the presence of a base. Examples of the base used in the reaction include organic bases such as triethylamine, tripropylamine, pyridine, dimethylaminopyridine and 1,8-diazabicyclo[5.4.0]-7-undecene; and inorganic bases such as sodium hydroxide, potassium hydroxide, calcium hydroxide, sodium carbonate, potassium carbonate, sodium hydrogen carbonate, calcium carbonate, sodium hydride, sodium methoxide, sodium ethoxide and potassium tert-butoxide. The amount of the base used in the reaction is usually 0.5 to 10 mol, preferably 1 to 5 mol per 1 mol of the compound of formula (II).

The reaction temperature is usually from −30 to 180° C. preferably from 0 to 100° C. The reaction time is usually from 10 minutes to 30 hours.

The progress of the reaction can be confirmed by analyzing a portion of the reaction mixture by thin layer chromatography or high performance liquid chromatography. After completion of the reaction, the compound represented by formula (I) can be isolated, for example, by mixing the reaction mixture with water followed by extraction with an organic solvent, and then drying and concentrating the resulting organic layer.

Production Process 2

A compound represented by formula (I-a), which is the compound of formula (I) of the present invention wherein n represents 1, 2, 3 or 4, one of $Z^2$s represents a $C_{3-8}$ cycloalkyl group, a $C_{6-10}$ aryl group or a 5- or 6-membered heteroaryl group (in which the $C_{3-8}$ cycloalkyl group, the $C_{6-10}$ aryl group and the 5- or 6-membered heteroaryl group may be substituted with at least one member selected from the group consisting of halogen and $C_{1-6}$ alkyl groups), and when n is 2, 3 or 4, other $Z^2$s are as defined above provided that halogen, a $C_{6-10}$ aryl group substituted with halogen and a 5- or 6-membered heteroaryl group substituted with halogen are excluded, can also be produced by the following reaction.

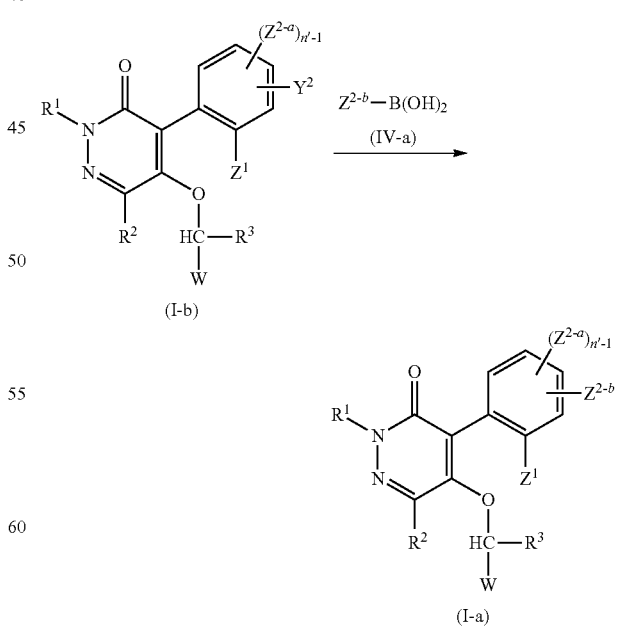

wherein $Y^2$ represents halogen; $Z^{2-a}$ is as defined above for $Z^2$ provided that halogen, a $C_{6-10}$ aryl group substituted with halogen and a 5- or 6-membered heteroaryl group substituted with halogen are excluded; $Z^{2-b}$ represents a $C_{3-8}$ cycloalkyl group, a $C_{6-10}$ aryl group or a 5- or 6-membered heteroaryl group (in which the $C_{3-8}$ cycloalkyl group, the $C_{6-10}$ aryl group and the 5- or 6-membered heteroaryl group may be substituted with at least one member selected from the group consisting of halogen and $C_{1-6}$ alkyl groups), $R^1$, $R^2$, $R^3$, W and $Z^1$ are as defined above, and n' represents 1, 2, 3 or 4.

The amount of the compound represented by formula (IV-a) used in the reaction is usually 1 mol or more, preferably 1 to 3 mol per 1 mol of the compound represented by formula (I-b).

The reaction is performed in a solvent. Examples of the solvent used in the reaction include aromatic hydrocarbons such as benzene, toluene and xylene; alcohols such as methanol, ethanol and propanol; ethers such as diethylether, diisopropylether, dioxane, tetrahydrofuran and dimethoxyethane; ketones such as acetone and methyl ethyl ketone; nitriles such as acetonitrile; amides such as dimethylformamide and dimethylacetamide; sulfoxides such as dimethyl sulfoxide; sulfones such as sulfolane; water; and mixtures thereof.

The reaction is performed in the presence of a base. Examples of the base used in the reaction include organic bases such as triethylamine, tripropylamine, pyridine, dimethylaniline, dimethylaminopyridine and 1,8-diazabicyclo[5.4.0]-7-undecene; and inorganic bases such as sodium hydroxide, potassium hydroxide, calcium hydroxide, sodium carbonate, potassium carbonate, sodium hydrogen carbonate, calcium carbonate, cesium carbonate and potassium phosphate. The amount of the base used in the reaction is usually 0.5 to 10 mol, preferably 1 to 5 mol per 1 mol of the compound represented by formula (I-b).

The reaction is usually performed in the presence of palladium catalyst such as tetrakis(triphenylphosphine)palladium, dichlorobis(triphenylphosphine)palladium or dichlorobis(tricyclohexylphosphine)palladium. The amount of the palladium catalyst used in the reaction is usually 0.001 to 0.5 mol, preferably 0.01 to 0.2 mol per 1 mol of the compound represented by formula (I-b).

The reaction temperature is usually from 20 to 180° C. and preferably from 60 to 150° C. The reaction time is usually from 30 minutes to 100 hours.

The progress of the reaction can be confirmed by analyzing a portion of the reaction mixture by thin layer chromatography or high performance liquid chromatography. After completion of the reaction, the compound represented by formula (I-a) can be isolated, for example, by mixing the reaction mixture with water followed by extraction with an organic solvent, and then drying and concentrating the resulting organic layer.

Production Process 3

A compound represented by formula (I-c), which is the compound of formula (I) wherein W is $S(O)R^5$, can be also produced by the following reaction.

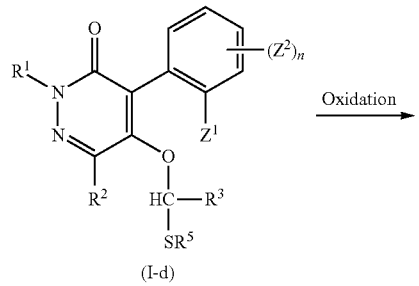

(I-d)

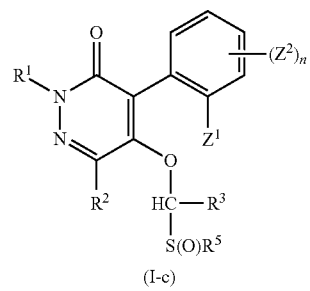

(I-c)

wherein $R^1$, $R^2$, $R^3$, $R^5$, $Z^1$, $Z^2$ and n are as defined above.

In the reaction, an oxidizing agent is used. Examples of the oxidizing agent include hydrogen peroxide; peracids such as peracetic acid, perbenzoic acid and m-chloro perbenzoic acid; sodium periodate, ozone, selenium dioxide, chromic acid, dinitrogen tetroxide, acetyl nitrate, iodine, bromine, NBS and iodosylbenzene. The amount of the oxidizing agent used in the reaction is usually 0.8 to 1.2 mol per 1 mol of the compound represented by formula (I-d).

The reaction is performed in a solvent. Examples of the solvent used in the reaction include saturated hydrocarbons such as hexane, heptane, octane and cyclohexane; aromatic hydrocarbons such as benzene, toluene, xylene, chlorobenzene and dichlorobenzene; halogenated saturated hydrocarbons such as dichloromethane, chloroform, 1,2-dichloroethane and carbon tetrachloride; alcohols such as methanol, ethanol and propanol; nitriles such as acetonitrile; amides such as dimethylformamide and dimethylacetamide; sulfones such as sulfolane; organic acids such as acetic acid and propionic acid; water; and mixtures thereof.

The reaction temperature is usually from −50 to 100° C., preferably from 0 to 50° C. The reaction time is usually from 10 minutes to 100 hours.

The progress of the reaction can be confirmed by analyzing a portion of the reaction mixture by thin layer chromatography or high performance liquid chromatography. After completion of the reaction, the compound represented by formula (I-c) can be isolated, for example, by mixing the reaction mixture with water followed by extraction with an organic solvent, and then drying and concentrating the resulting organic layer.

Production Process 4

A compound represented by formula (I-e), which is the compound of formula (I) wherein W represents $S(O)_2R^5$, can also be produced by the following reaction.

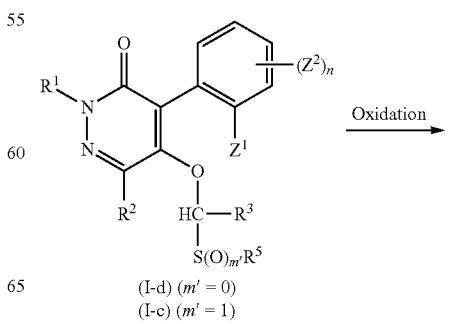

(I-d) (m' = 0)
(I-c) (m' = 1)

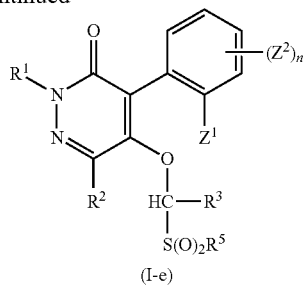

(I-e)

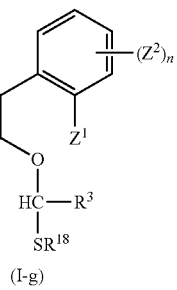

(I-g)

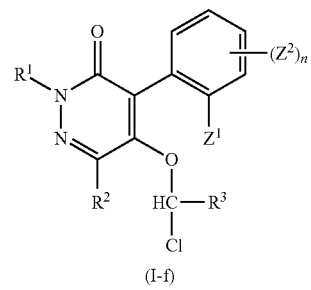

(I-f)

wherein m' represents 0 or 1, and $R^1$, $R^2$, $R^3$, $R^5$, $Z^1$, $Z^2$ and n are as defined above.

In the reaction, an oxidizing agent is used. Examples of the oxidizing agent include hydrogen peroxide; peracids such as peracetic acid, perbenzoic acid and m-chloroperbenzoic acid; sodium periodate, ozone, selenium dioxide, chromic acid, dinitrogen tetroxide, acetyl nitrate, iodine, bromine, NBS, iodosylbenzene, a combination of hydrogen peroxide and a tungsten catalyst, a combination of hydrogen peroxide and a vanadium catalyst, and potassium permanganate.

When the compound represented by formula (I-d) is used as a starting material, the amount of the oxidizing agent used in the reaction is usually 2 to 10 mol, preferably 2 to 4 mol per 1 mol of the compound represented by formula (I-d). When the compound represented by formula (I-c) is used as a starting material, the amount of the oxidizing agent used in the reaction is usually 1 to 10 mol, preferably 1 to 3 mol per 1 mol of the compound represented by formula (I-c).

The reaction is performed in a solvent. Examples of the solvent used in the reaction include saturated hydrocarbons such as hexane, heptane, octane and cyclohexane; aromatic hydrocarbons such as benzene, toluene, xylene, chlorobenzene and dichlorobenzene; halogenated saturated hydrocarbons such as dichloromethane, chloroform, 1,2-dichloroethane and carbon tetrachloride; alcohols such as methanol, ethanol and propanol; nitriles such as acetonitrile; amides such as dimethylformamide and dimethylacetamide; sulfones such as sulfolane; organic acids such as acetic acid and propionic acid; water; and mixtures thereof.

The reaction temperature is usually from 0 to 200° C., preferably from 20 to 150° C. The reaction time is usually from 30 minutes to 100 hours.

The progress of the reaction can be confirmed by analyzing a portion of the reaction mixture by thin layer chromatography or high performance liquid chromatography. After completion of the reaction, the compound represented by formula (I-e) can be isolated, for example, by mixing the reaction mixture with water followed by extraction with an organic solvent, and then drying and concentrating the resulting organic layer.

Production Process 5

A compound represented by formula (I-f), which is the compound of formula (I) wherein W represents chlorine, can also be produced by the following reaction.

wherein $R^{18}$ represents a $C_{1-6}$ alkyl group, and $R^1$, $R^2$, $R^3$, $Z^1$ $Z^2$ and n are as defined above.

In this reaction, a chlorinating agent is used. Examples of the chlorinating agent include sulfuryl chloride. The amount of the chlorinating agent used in the reaction is usually 0.8 to 1.2 mol per 1 mol of the compound represented by formula (I-g).

The reaction is performed in a solvent. Examples of the solvent used in the reaction include halogenated hydrocarbons such as dichloromethane, chloroform and 1,2-dichloroethane.

The reaction temperature is usually from −100 to 50° C., preferably from −80 to 30° C. The reaction time is usually from 10 minutes to 30 hours.

The progress of the reaction can be confirmed by analyzing a portion of the reaction mixture by thin layer chromatography or high performance liquid chromatography.

After the completion of the reaction, the compound represented by formula (I-f) can be isolated, for example, by subjecting the reaction mixture to concentration, chromatographic purification and the like.

Specific examples of the compound of the present invention include:

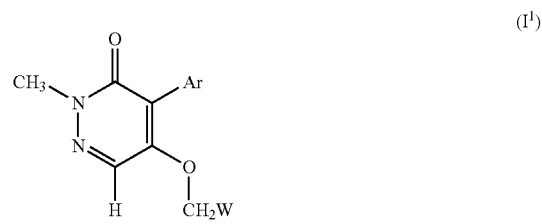

(I¹)

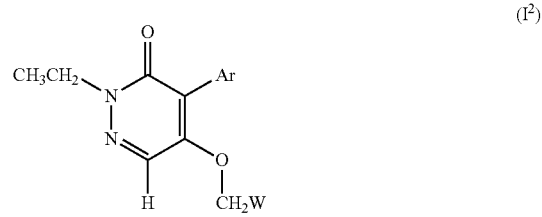

(I²)

-continued
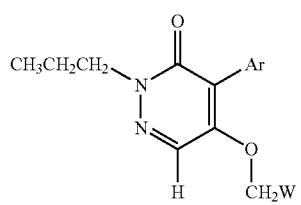
(I³)
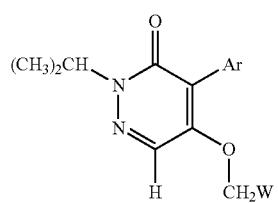
(I⁴)
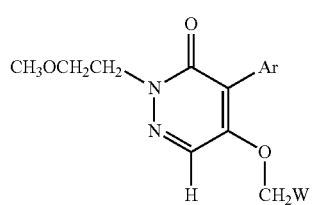
(I⁵)
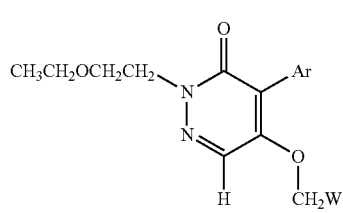
(I⁶)
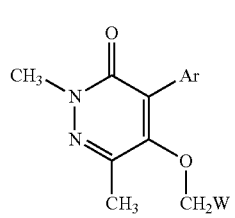
(I⁷)
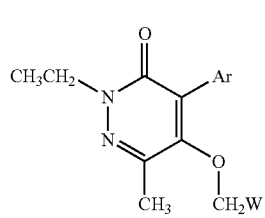
(I⁸)
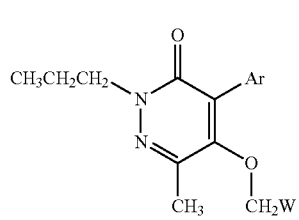
(I⁹)
-continued
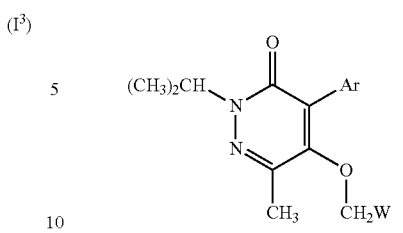
(I¹⁰)
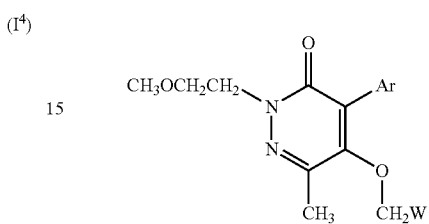
(I¹¹)
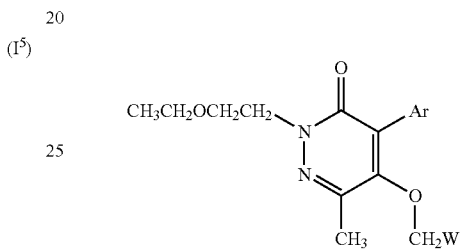
(I¹²)
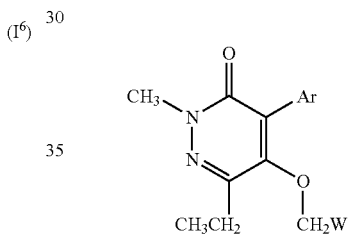
(I¹³)
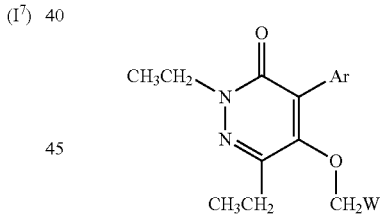
(I¹⁴)
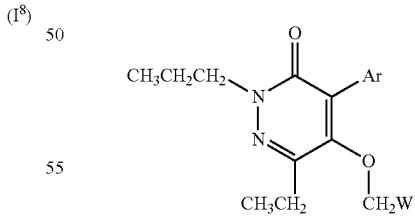
(I¹⁵)
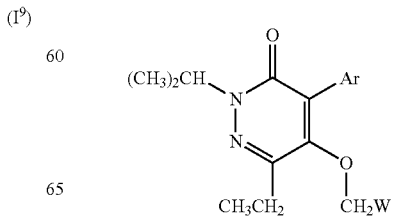
(I¹⁶)

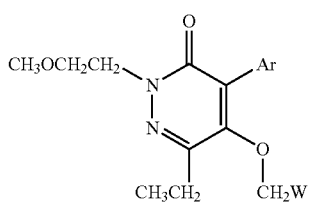 (I¹⁷)
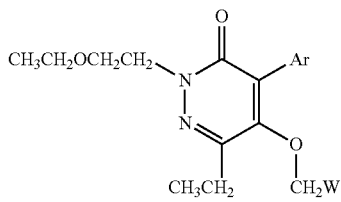 (I¹⁸)
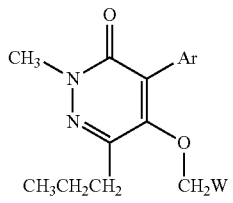 (I¹⁹)
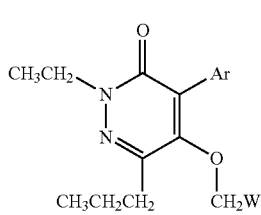 (I²⁰)
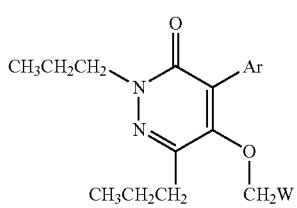 (I²¹)
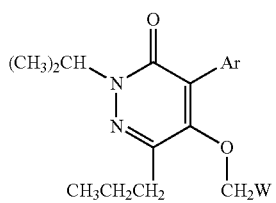 (I²²)
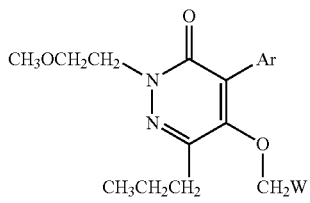 (I²³)
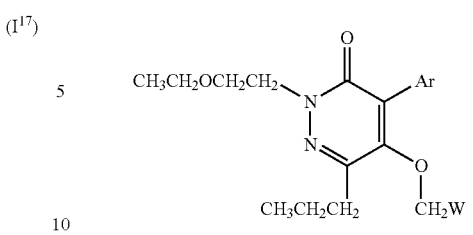 (I²⁴)
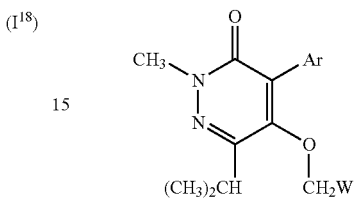 (I²⁵)
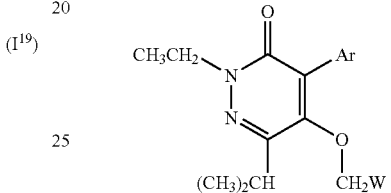 (I²⁶)
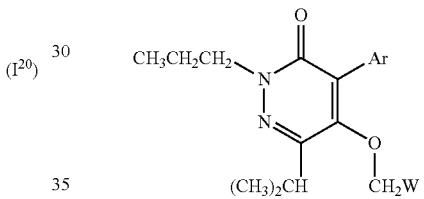 (I²⁷)
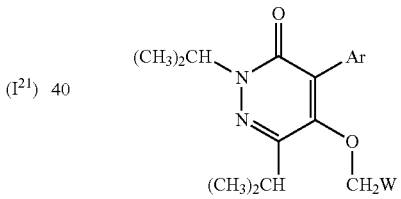 (I²⁸)
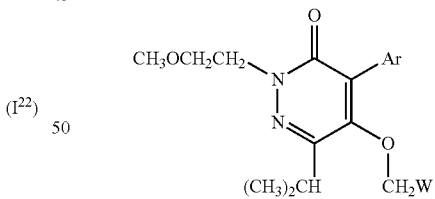 (I²⁹)
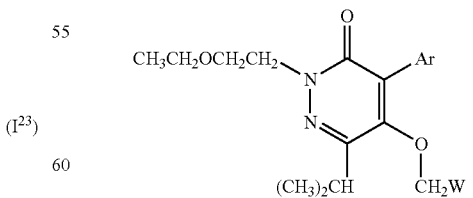 (I³⁰)
1) a pyridazinone compound represented by any of formulas (I¹) to (I³⁰), wherein Ar is a 2-ethylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;
2) a pyridazinone compound represented by any of formulas ($I^1$) to ($I^{30}$), wherein Ar is a 2-propylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;
3) a pyridazinone compound represented by any of formulas ($I^1$) to ($I^{30}$), wherein Ar is a 2,4-dimethylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;
4) a pyridazinone compound represented by any of formulas ($I^1$) to ($I^{30}$), wherein Ar is a 2,6-dimethylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;
5) a pyridazinone compound represented by any of formulas ($I^1$) to ($I^{30}$), wherein Ar is a 2-ethyl-4-methylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;
6) a pyridazinone compound represented by any of formulas ($I^1$) to ($I^{30}$), wherein Ar is a 2-ethyl-6-methylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;
7) a pyridazinone compound represented by any of formulas ($I^1$) to ($I^{30}$), wherein Ar is a 2,6-diethylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;
8) a pyridazinone compound represented by any of formulas ($I^1$) to ($I^{30}$), wherein Ar is a 2,4,6-trimethylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;
9) a pyridazinone compound represented by any of formulas ($I^1$) to ($I^{30}$), wherein Ar is a 2-ethyl-4,6-dimethylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;
10) a pyridazinone compound represented by any of formulas ($I^1$) to ($I^{30}$), wherein Ar is a 2,6-diethyl-4-methylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;
11) a pyridazinone compound represented by any of formulas ($I^1$) to ($I^{30}$), wherein Ar is a 2,4,6-triethylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;
12) a pyridazinone compound represented by any of formulas ($I^1$) to ($I^{30}$), wherein Ar is a 2,4-diethylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;
13) a pyridazinone compound represented by any of formulas ($I^1$) to ($I^{30}$), wherein Ar is a 2,4-diethyl-6-methylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;
14) a pyridazinone compound represented by any of formulas ($I^1$) to ($I^{30}$), wherein Ar is a 4-chloro-2,6-diethylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;
15) a pyridazinone compound represented by any of formulas ($I^1$) to ($I^{30}$), wherein Ar is a 4-bromo-2,6-diethylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;
16) a pyridazinone compound represented by any of formulas ($I^1$) to ($I^{30}$), wherein Ar is a 4-cyano-2,6-diethylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;
17) a pyridazinone compound represented by any of formulas ($I^1$) to ($I^{30}$), wherein Ar is a 2,6-diethyl-4-methoxyphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;
18) a pyridazinone compound represented by any of formulas ($I^1$) to ($I^{30}$), wherein Ar is a 2,6-diethyl-4-nitrophenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;
19) a pyridazinone compound represented by any of formulas ($I^1$) to ($I^{30}$), wherein Ar is a 2,6-diethyl-4-phenylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;
20) a pyridazinone compound represented by any of formulas ($I^1$) to ($I^{30}$), wherein Ar is a 2,6-diethyl-4-ethynylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;

21) a pyridazinone compound represented by any of formulas ($I^1$) to ($I^{30}$), wherein Ar is a 2-cyano-4,6-dimethylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;

22) a pyridazinone compound represented by any of formulas ($I^1$) to ($I^{30}$), wherein Ar is a 2-cyano-6-ethyl-4-methylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;

23) a pyridazinone compound represented by any of formulas ($I^1$) to ($I^{30}$), wherein Ar is a 2,4-dichloro-6-methylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;

24) a pyridazinone compound represented by any of formulas ($I^1$) to ($I^{30}$), wherein Ar is a 2-chloro-4,6-dimethylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;

25) a pyridazinone compound represented by any of formulas ($I^1$) to ($I^{30}$), wherein Ar is a 2-chloro-6-ethyl-4-methylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;

26) a pyridazinone compound represented by any of formulas ($I^1$) to ($I^{30}$), wherein Ar is a 2,4-dichloro-6-ethylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;

27) a pyridazinone compound represented by any of formulas ($I^1$) to ($I^{30}$), wherein Ar is a 2-bromo-6-ethyl-4-methylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;

28) a pyridazinone compound represented by any of formulas ($I^1$) to ($I^{30}$), wherein Ar is a 4-chloro-2-ethyl-6-methoxyphenyl group, and W is chlorine, a methoxy group, an ethoxy group, a propyloxy group, an isopropyloxy group, a benzyloxy group, a methylthio group, an ethylthio group, methylsulfinyl group, a methylsulfonyl group or an N-phenyl-N-ethoxycarbonylamino group;

29) a pyridazinone compound represented by any of formulas ($I^1$) to ($I^{30}$), wherein Ar is a 2-ethyl-6-methoxy-4-methylphenyl group, and W is chlorine, a methoxy group, an ethoxy group, a propyloxy group, an isopropyloxy group, a benzyloxy group, a methylthio group, an ethylthio group, methylsulfinyl group, a methylsulfonyl group or an N-phenyl-N-ethoxycarbonylamino group;

30) a pyridazinone compound represented by any of formulas ($I^1$) to ($I^{30}$), wherein Ar is a 4-(4-chlorophenyl)-2,6-diethylphenyl group, and W is chlorine, a methoxy group, an ethoxy group, a propyloxy group, an isopropyloxy group, benzyloxy group, a methylthio group, an ethylthio group, a methylsulfinyl group, a methylsulfonyl group or an N-phenyl-N-ethoxycarbonylamino group;

31) a pyridazinone compound represented by any of formulas ($I^1$) to ($I^{30}$), wherein Ar is a 2,6-diethyl-4-(4-methylphenyl)phenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;

32) a pyridazinone compound represented by any of formulas ($I^1$) to ($I^{30}$), wherein Ar is a 2-ethyl-6-ethynyl-4-phenylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;

33) a pyridazinone compound represented by any of formulas ($I^1$) to ($I^{30}$), wherein Ar is a 2-ethyl-6-methoxy-4-phenylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;

34) a pyridazinone compound represented by any of formulas ($I^1$) to ($I^{30}$), wherein Ar is a 2-chloro-6-ethyl-4-phenylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;

35) a pyridazinone compound represented by any of formulas ($I^1$) to ($I^{30}$), wherein Ar is a 2,6-diethyl-4-trifluoromethylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;

36) a pyridazinone compound represented by any of formulas ($I^1$) to ($I^{30}$), wherein Ar is a 2,6-diethyl-4-trifluoromethoxyphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;

37) a pyridazinone compound represented by any of formulas ($I^1$) to ($I^{30}$), wherein Ar is a 2-ethyl-6-ethynyl-4-methylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;

38) a pyridazinone compound represented by any of formulas ($I^1$) to ($I^{30}$), wherein Ar is a 2-chloro-6-ethyl-4-methoxyphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;

39) a pyridazinone compound represented by any of formulas ($I^1$) to ($I^{30}$), wherein Ar is a 2-cyclopropyl-6-ethyl-4-methylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;

40) a pyridazinone compound represented by any of formulas ($I^1$) to ($I^{30}$), wherein Ar is a 4-cyclopropyl-2,6-diethylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;

41) a pyridazinone compound represented by any of formulas ($I^1$) to ($I^{30}$), wherein Ar is a 5-(4-chlorophenyl)-2-methylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;

42) a pyridazinone compound represented by any of formulas ($I^1$) to ($I^{30}$), wherein Ar is a 5-(4-fluorophenyl)-2-methylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;

43) a pyridazinone compound represented by any of formulas ($I^1$) to ($I^{30}$), wherein Ar is a 2-bromo-4,6-dimethylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group;

44) a pyridazinone compound represented by any of formulas ($I^1$) to ($I^{30}$), wherein Ar is a 2-methoxy-4,6-dimethylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group; and 45) a pyridazinone compound represented by any of formulas ($I^1$) to ($I^{30}$), wherein Ar is a 2-ethynyl-4,6-dimethylphenyl group, and W is chlorine, a methoxy group, an ethoxy group, a propyloxy group, an isopropyloxy group, a benzyloxy group, a methylthio group, an ethylthio group, a methylsulfinyl group, a methylsulfonyl group or an N-phenyl-N-ethoxycarbonylamino group.

Reference Production Process 1

The compound represented by formula (II) can be produced by reacting a compound represented by formula (V) with a metal hydroxide.

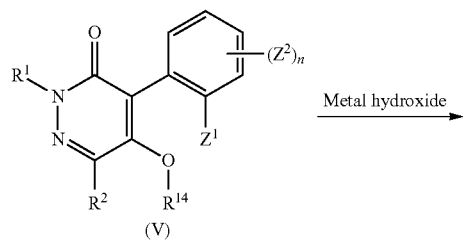

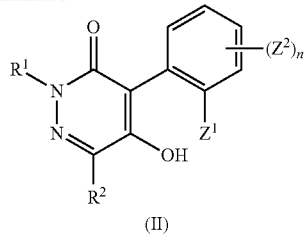

wherein $R^{14}$ represents a $C_{1-6}$ alkyl group, and $R^1$, $R^2$, $Z^1$, $Z^2$ and n are as defined above.

The reaction is usually performed in a solvent. Examples of the solvent used in the reaction include water; ethers such as tetrahydrofuran and dioxane; and mixtures thereof.

Examples of the metal hydroxide used in the reaction include hydroxides of alkali metals such as sodium hydroxide and potassium hydroxide. The amount of the metal hydroxide used in the reaction is usually from 1 to 120 mol, preferably from 1 to 40 mol per 1 mol of the compound represented by formula (V).

The reaction temperature is usually from room temperature to the boiling point of a solvent, preferably the boiling point of a solvent. The reaction can be also performed in a sealed tube or a high pressure resistant closed vessel while heating. The reaction time is usually from about 5 minutes to several weeks.

The progress of the reaction can be confirmed by analyzing a portion of the reaction mixture by thin layer chromatography or high performance liquid chromatography. After completion of the reaction, the compound represented by formula (II) can be isolated, for example, by neutralizing the reaction mixture with an addition of an acid, mixing the reaction mixture with water followed by extraction with an organic solvent, and then drying and concentrating the resulting organic layer.

Reference Production Process 2

The compound represented by formula (II) can also be produced by reacting the compound represented by formula (V) with an acid.

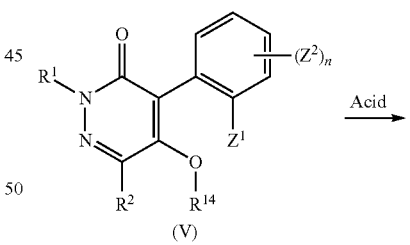

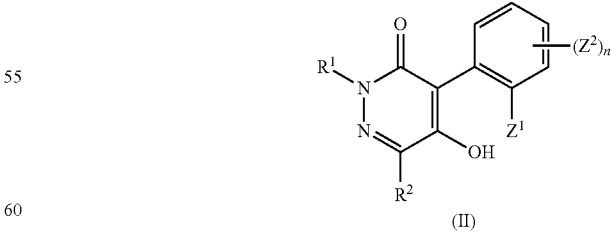

wherein $R^1$, $R^2$, $R^{14}$, $Z^1$, $Z^2$ and n are as defined above.

The reaction is usually performed in a solvent. Examples of the solvent used in the reaction include water; organic carboxylic acids such as acetic acid and propionic acid; and mixtures thereof.

Examples of the acid used in the reaction include hydrobromic acid and trifluoromethanesulfonic acid. The amount of the acid used in the reaction is usually 1 to 120 mol, preferably 2 to 20 mol per 1 mol of the compound represented by formula (V).

The reaction temperature is usually from room temperature to the boiling point of a solvent to be used, preferably from 80° C. to the boiling point of the solvent. The reaction can be also performed in a sealed tube or a high pressure resistant closed vessel while heating. The reaction time is usually from about 5 minutes to several weeks.

The progress of the reaction can be confirmed by analyzing a portion of the reaction mixture by thin layer chromatography or high performance liquid chromatography. After completion of the reaction, the compound represented by formula (II) can be isolated, for example, by mixing the reaction mixture with water followed by extraction with an organic solvent, and then drying and concentrating the resulting organic layer.

The compound represented by formula (II) can be also produced by the reaction of the compound represented by formula (V) with a Lewis acid, followed by the reaction with aqueous solution of an alkali.

The reaction is performed in a solvent. Examples of the solvent used in the reaction include halogenated hydrocarbons such as dichloromethane, chloroform and 1,2-dichloroethane.

Examples of the Lewis acid used in the reaction include boron tribromide and aluminum chloride. The amount of the Lewis acid used in the reaction is usually from 1 to 10 mol, preferably from 1 to 3 mol per 1 mol of the compound represented by formula (V).

Examples of the alkali used in the reaction include alkali metal hydroxide or alkaline earth metal hydroxide such as sodium hydroxide, potassium hydroxide and calcium hydroxide. The amount of the alkali used in the reaction is usually from 1 to 10 mol per 1 mol of the compound represented by formula (V).

The reaction temperature is usually from −50 to 100° C., preferably from 0 to 30° C. The reaction time is usually from about 5 minutes to 10 hours.

The progress of the reaction can be confirmed by analyzing a portion of the reaction mixture by thin layer chromatography or high performance liquid chromatography. After completion of the reaction, the compound represented by formula (II) can be isolated, for example, by mixing the reaction mixture with acid and water followed by extraction with an organic solvent, and then drying and concentrating the resulting organic layer.

Reference Production Process 3

The compound represented by formula (II) can be produced by reacting a compound represented by formula (VI) with a base.

wherein $R^{15}$ represents a $C_{1-6}$ alkyl group, and $R^1$, $R^2$, $Z^1$, $Z^2$ and n are as defined above.

The reaction is usually performed in a solvent. Examples of the solvent used in the reaction include aromatic hydrocarbons such as benzene, toluene and xylene; ethers such as diethylether, diisopropylether, dioxane, tetrahydrofuran and dimethoxyethane; halogenated hydrocarbons such as dichloromethane, chloroform and 1,2-dichloroethane; nuitriles such as acetonitrile; amides such as dimethylformamide and dimethylacetamide; sulfoxides such as dimethyl sulfoxide; sulfones such as sulfolane; and mixtures thereof.

Examples of the base used in the reaction include metal alkoxides such as potassium tert-butoxide; alkali metal hydride such as sodium hydride; and organic bases such as triethylamine, tributylamine and N,N-diisopropylethylamine. The amount of the base used in the reaction is usually from 1 to 10 mol, preferably from 2 to 5 mol per 1 mol of the compound represented by formula (VI).

The reaction temperature is usually from −60 to 180° C., and preferably from −10 to 100° C. The reaction time is usually from 10 minutes to 30 hours.

The progress of the reaction can be confirmed by analyzing a portion of the reaction mixture by thin layer chromatography or high performance liquid chromatography. After completion of the reaction, the compound represented by formula (II) can be isolated, for example, by mixing the reaction mixture with water and an acid, followed by extraction with an organic solvent, and then drying and concentrating the resulting organic layer.

Reference Production Process 4

A compound represented by formula (II-a), which is the compound of formula (II) wherein n represents 1, 2, 3 or 4, one of $Z^2$s represents a $C_{3-8}$ cycloalkyl group, a $C_{6-10}$ aryl group or a 5- or 6-membered heteroaryl group (in which the $C_{3-8}$ cycloalkyl group, the $C_{6-10}$ aryl group and the 5- or 6-membered heteroaryl group may be substituted with at least one member selected from the group consisting of halogen and $C_{1-6}$ alkyl groups), and when n is 2, 3 or 4, other $Z^2$s are as defined above provided that halogen, a $C_{6-10}$ aryl group substituted with halogen and a 5- or 6-membered heteroaryl group substituted with halogen are excluded, can also be produced by the following reaction.

-continued

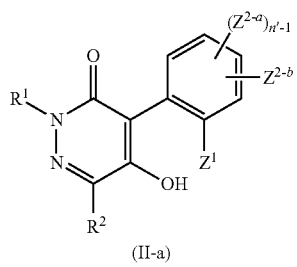

(II-a)

wherein $R^1$, $R^2$, $Z^1$, $Z^{2-a}$, $Z^{2-b}$, $Y^2$ and n' are as defined above.

The amount of the compound represented by formula (IV-a) used in the reaction is usually 1 mol or more, preferably 1 to 3 mol per 1 mol of the compound represented by formula (II-b).

The reaction is performed in a solvent. Examples of the solvent used in the reaction include aromatic hydrocarbons such as benzene, toluene and xylene; alcohols such as methanol, ethanol and propanol; ethers such as diethylether, diisopropylether, dioxane, tetrahydrofuran and dimethoxyethane; ketones such as acetone and methyl ethyl ketone; nitriles such as acetonitrile; amides such as dimethylformamide and dimethylacetamide; sulfoxides such as dimethyl sulfoxide; sulfones such as sulfolane; water; and mixtures thereof.

The reaction is performed in the presence of a base. Examples of the base used in the reaction include organic bases such as triethylamine, tripropylamine, pyridine, dimethylaniline, dimethylaminopyridine and 1,8-diazabicyclo[5.4.0]-7-undecene; and inorganic bases such as sodium hydroxide, potassium hydroxide, calcium hydroxide, sodium carbonate, potassium carbonate, sodium hydrogen carbonate, calcium carbonate, cesium carbonate and potassium phosphate. The amount of the base used in the reaction is usually 0.5 to 10 molar equivalents, preferably 1 to 5 molar equivalents to 1 mol of the compound represented by formula (II-b).

The reaction is usually performed in the presence of a palladium catalyst such as tetrakis(triphenylphosphine)palladium, dichlorobis(triphenylphosphine)palladium or dichlorobis(tricyclohexylphosphine)palladium. The amount of the palladium catalyst used in the reaction is usually 0.001 to 0.5 mol, preferably 0.01 to 0.2 mol per 1 mol of the compound represented by formula (II-b).

The reaction temperature is usually from 20 to 180° C. and preferably from 60 to 150° C. The reaction time is usually from 30 minutes to 100 hours.

The progress of the reaction can be confirmed by analyzing a portion of the reaction mixture by thin layer chromatography or high performance liquid chromatography. After completion of the reaction, the compound represented by formula (II-a) can be isolated, for example, by mixing the reaction mixture with water and an acid, followed by extraction with an organic solvent, and then drying and concentrating the resulting organic layer.

Reference Production Process 5

Among the compounds represented by formula (II), compound represented by the following formula (II-c) can be also produced by the following reaction.

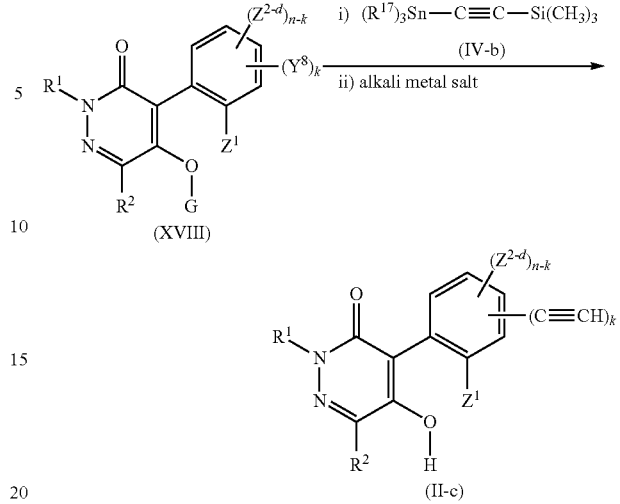

wherein $Y^8$ represents halogen (for example, chlorine, bromine, or iodine); $R^{17}$ represents a $C_{1-6}$ alkyl group (for example, a methyl group, or a butyl group); $Z^{2-d}$ is as defined for $Z^2$, provided that a $C_{2-6}$ alkynyl group, halogen, a $C_{6-10}$ aryl group substituted with at least one halogen and a 5- or 6-membered heteroaryl group substituted with at least one halogen are excluded; k represents 1, 2, 3 or 4; G represents a $C_{1-6}$ alkylcarbonyl group or a $C_{1-6}$ alkyloxycarbonyl group; and $R^1$, $R^2$, $Z^1$ and n are as defined above.

In the reaction, a compound represented by formula (XVIII) and an organometallic reagent represented by formula (IV-b) are subjected to coupling reaction, followed by reaction with an alkali metal salt to remove a trimethylsilyl group and to convert the substituent G into hydrogen. Thus the compound represented by formula (II-c) can be prepared.

The first step of the reaction using the compound represented by formula (IV-b) is performed in a solvent. Examples of the solvent include aromatic hydrocarbons such as benzene and toluene; ethers such as diethyl ether, diisopropyl ether, dioxane, tetrahydrofuran and dimethoxyethane; halogenated hydrocarbons such as chloroform and 1,2-dichloroethane; amides such as dimethylformamide, dimethylacetamide; and a mixture thereof.

In the first step of the reaction, the organometallic reagent represented by formula (IV-b) can be usually used in an amount of k molar equivalents or more, preferably 1 to 10 molar equivalents to the compound represented by formula (XVIII).

The first step of the reaction is carried out in the presence of a catalyst. Examples of the catalyst include palladium catalysts such as tetrakis(triphenylphosphine)palladium and dichlorobis(triphenylphosphine)palladium. The amount of the catalyst used in the reaction is usually 0.001 to 0.5 molar equivalents, preferably 0.01 to 0.2 molar equivalents to the compound represented by formula (XVIII).

The reaction temperature of the first step of the reaction is usually at −80 to 180° C., preferably at −30 to 150° C. The reaction time of the first step of the reaction is usually from 30 minutes to 100 hours.

The completion of the reaction can be confirmed by an analytical means such as thin layer chromatography, high performance liquid chromatography or the like after sampling a part of a reaction mixture. After the completion of the reaction, a product from the first step of the reaction can be isolated, for example, by subjecting the reaction mixture to concentration, chromatographic purification and the like.

The second step of the reaction using an alkali metal salt is carried out in a solvent. Examples of the solvent include water; alcohols such as methanol and ethanol; ethers such as dioxane, tetrahydrofuran and dimethoxyethane; and a mixture thereof.

Examples of the alkali metal salt used for the second step of the reaction include alkali metal hydroxides such as sodium hydroxide and potassium hydroxide; and alkali metal carbonates such as sodium carbonate and potassium carbonate. In the second step of the reaction, the amount of the alkali metal salt is usually (1+k) molar equivalents or more, preferably 2 to 10 molar equivalents to the compound represented by formula (XVIII).

The reaction temperature of the second step of the reaction is usually at −30 to 180° C., preferably at −10 to 50° C. The reaction time of the second step of the reaction is usually from 30 minutes to 100 hours.

The completion of the reaction can be confirmed by an analytical means such as thin layer chromatography, high performance liquid chromatography or the like after sampling a part of a reaction mixture. After the completion of the reaction, the compound represented by formula (II-c) can be isolated, for example, by mixing the reaction mixture with water, neutralizing the reaction mixture with an addition of an acid followed by extraction with an organic solvent, and then drying and concentrating the resulting organic layer.

Reference Production Process 6

The compound represented by formula (V) can be produced, for example, by the following reaction.

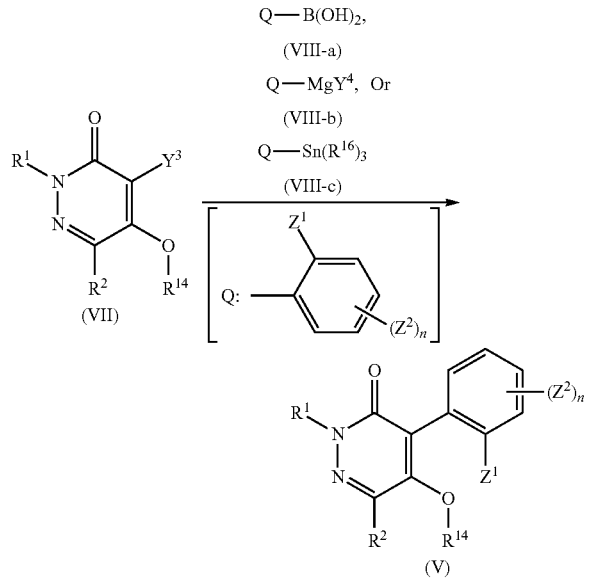

wherein $Y^3$ represents a leaving group (for example, halogen), $Y^4$ represents halogen, $R^{16}$ represents a $C_{1-6}$ alkyl group (for example, a methyl group, or a butyl group), and $R^1$, $R^2$, $R^{14}$, $Z^1$, $Z^2$ and n are as defined above.

Reaction of the Compound of Formula (VII) with the Compound of Formula (VIII-a):

The reaction is performed in a solvent. Examples of the solvent used in the reaction include aromatic hydrocarbons such as benzene, toluene and xylene; alcohols such as methanol, ethanol and propanol; ethers such as diethylether, diisopropylether, dioxane, tetrahydrofuran and dimethoxyethane; ketones such as acetone and methyl ethyl ketone; nitriles such as acetonitrile; amides such as dimethylformamide and dimethylacetamide; sulfoxides such as dimethyl sulfoxide; sulfones such as sulfolane; water; and mixtures thereof.

The reaction is performed in the presence of a base. Examples of the base used in the reaction include organic bases such as triethylamine, tripropylamine, pyridine, dimethylaniline, dimethylaminopyridine and 1,8-diazabicyclo [5.4.0]-7-undecene; and inorganic bases such as sodium hydroxide, potassium hydroxide, calcium hydroxide, sodium carbonate, potassium carbonate, sodium hydrogen carbonate, calcium carbonate, cesium carbonate and potassium phosphate. The amount of the base used in the reaction is usually from 0.5 to 10 mol, preferably from 1 to 5 mol per 1 mol of the compound represented by formula (VII).

The reaction is usually performed in the presence of a palladium catalyst such as tetrakis(triphenylphosphine)palladium or dichlorobis(triphenylphosphine)palladium. The amount of the catalyst used in the reaction is usually from 0.001 to 0.5 mol, preferably from 0.01 to 0.2 mol per 1 mol of the compound represented by formula (VII). The reaction can also be performed in the presence of a quaternary ammonium salt. Examples of the quaternary ammonium salt used in the reaction include tetrabutylammonium bromide.

The amount of the compound represented by formula (VIII-a) used in the reaction is usually from 1 mol or more, preferably 1 to 3 mol per 1 mol of the compound represented by formula (VII).

The reaction temperature is usually from 20 to 180° C., preferably from 60 to 150° C. The reaction time is usually from 30 minutes to 100 hours. The progress of the reaction can be confirmed by analyzing a portion of the reaction mixture by thin layer chromatography or high performance liquid chromatography. After completion of the reaction, the compound represented by formula (V) can be isolated, for example, by mixing the reaction mixture with water followed by extraction with an organic solvent, and then drying and concentrating the resulting organic layer.

Reaction of the Compound of Formula (VII) with the Compound of Formula (VIII-b):

The reaction is performed in a solvent. Examples of the solvent used in the reaction include aromatic hydrocarbons such as benzene, toluene and xylene; ethers such as diethylether, diisopropylether, dioxane, tetrahydrofuran and dimethoxyethane; and mixtures thereof.

The reaction is usually performed in the presence of a nickel catalyst such as dichlorobis(1,3-diphenylphosphino) propane nickel or dichlorobis(triphenylphosphine)nickel; or a palladium catalyst such as tetrakis(triphenylphosphine)palladium or dichlorobis(triphenylphosphine)palladium. The amount of the catalyst used in the reaction is usually from 0.001 to 0.5 mol, preferably from 0.01 to 0.2 mol per 1 mol of the compound represented by formula (VII).

The amount of the compound represented by formula (VIII-b) used in the reaction used is usually 1 mol or more, preferably from 1 to 3 mol per 1 mol of the compound represented by formula (VII).

The reaction temperature is usually from −80 to 180° C., preferably from −30 to 150° C. The reaction time is usually 30 minutes to 100 hours. The progress of the reaction can be confirmed by analyzing a portion of the reaction mixture by thin layer chromatography or high performance liquid chromatography. After completion of the reaction, the compound represented by formula (V) can be isolated, for example, by mixing the reaction mixture with water followed by extraction with an organic solvent, and then drying and concentrating the resulting organic layer.

Reaction of the Compound of Formula (VII) with the Compound of Formula (VIII-C):

The reaction is performed in a solvent. Examples of the solvent used in the reaction include aromatic hydrocarbons such as benzene, toluene and xylene; ethers such as diethylether, diisopropylether, dioxane, tetrahydrofuran and dimethoxyethane; halogenated hydrocarbons such as chloroform and 1,2-dichloroethane; amides such as dimethylformamide and dimethylacetamide; and mixtures thereof.

The reaction is usually performed in the presence of a palladium catalyst such as tetrakis(triphenylphosphine)palladium or dichlorobis(triphenylphosphine)palladium. The amount of the catalyst used in the reaction is usually from 0.001 to 0.5 mol, preferably from 0.01 to 0.2 mol per 1 mol of the compound represented by formula (VII).

The amount of the compound represented by formula (VIII-c) used in the reaction is usually 1 mol or more, preferably from 1 to 3 mol per 1 mol of the compound represented by formula (VII).

The reaction temperature is usually from −80 to 180° C., preferably from −30 to 150° C. The reaction time is usually from 30 minutes to 100 hours.

The progress of the reaction can be confirmed by analyzing a portion of the reaction mixture by thin layer chromatography or high performance liquid chromatography. After completion of the reaction, the compound represented by formula (V) can be isolated, for example, by mixing the reaction mixture with water followed by extraction with an organic solvent, and then drying and concentrating the resulting organic layer.

Reference Production Process 7

The compound represented by formula (VI) can be produced, for example, by reacting a compound represented by formula (IX) with a compound represented by formula (X).

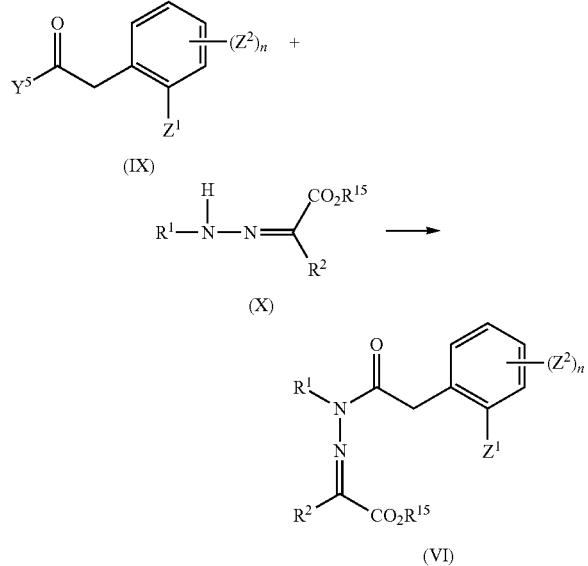

wherein $Y^5$ represents halogen, and $R^1$, $R^2$, $R^{15}$, $Z^1$, $Z^2$ and n are as defined above.

The reaction is usually performed in a solvent. Examples of the solvent used in the reaction include aromatic hydrocarbons such as benzene, toluene and xylene; ethers such as diethylether, diisopropylether, dioxane, tetrahydrofuran and dimethoxyethane; halogenated hydrocarbons such as dichloromethane, chloroform and 1,2-dichloroethane; ketones such as acetone and methyl ethyl ketone; nitriles such as acetonitrile; amides such as dimethylformamide and dimethylacetamide; sulfones such as sulfolane and mixtures thereof.

The reaction is usually performed in the presence of a base. Examples of the base used in the reaction include organic bases such as triethylamine, tripropylamine, pyridine, dimethylaminopyridine, 1,8-diazabicyclo[5.4.0]-7-undecene and 1,4-diazabicyclo[2.2.2]octane; and inorganic bases such as sodium hydroxide, potassium hydroxide, calcium hydroxide, sodium carbonate, potassium carbonate, sodium hydrogen carbonate, calcium carbonate and sodium hydride.

The amount of the compound represented by formula (X) used in the reaction is usually 0.5 mol or more, preferably from 0.8 to 2 mol per 1 mol of the compound represented by formula (IX). The amount of the base used in the reaction is usually 0.5 to 10 molar equivalents, preferably 1 to 5 molar equivalents to 1 mol of the compound represented by formula (IX).

The reaction temperature is usually from −30 to 180° C., preferably from −10 to 50° C. The reaction time is usually from 10 minutes to 30 hours.

The progress of the reaction can be confirmed by analyzing a portion of the reaction mixture by thin layer chromatography or high performance liquid chromatography. After completion of the reaction, the compound represented by formula (VI) can be isolated, for example, by mixing the reaction mixture with water followed by extraction with an organic solvent, and then drying and concentrating the resulting organic layer.

Reference Production Process 8

The compound represented by formula (IX) can be produced, for example, by the following Production Process.

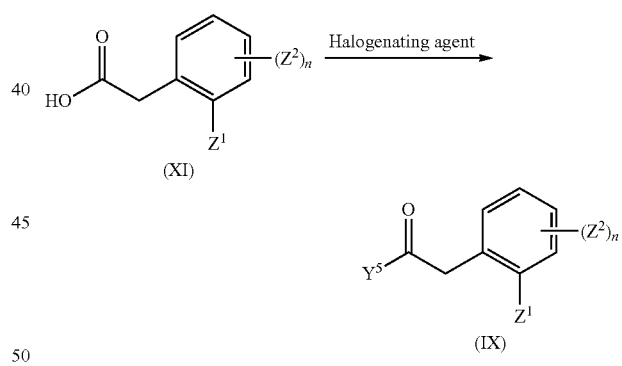

wherein $Z^1$, $Z^2$, $Y^5$ and n are as defined above.

Examples of the compound of formula (XI) include 2,4,6-trimethylphenylacetic acid, 2,4,6-triethylphenylacetic acid, 2,6-diethyl-4-methylphenylacetic acid, 2-ethylphenylacetic acid, 2-ethyl-4-methylphenylacetic acid, 2-ethyl-4,6-dimethylphenylacetic acid, 2,4-diethylphenylacetic acid, 2,6-diethylphenylacetic acid, 2,4-diethyl-6-methylphenylacetic acid, 4-chloro-2,6-diethylphenylacetic acid, 4-bromo-2,6-diethylphenylacetic acid, 4-cyano-2,6-diethylphenylacetic acid, 2,6-diethyl-4-methoxyphenylacetic acid, 2,6-diethyl-4-phenylphenylacetic acid, 4-(4-chlorophenyl)-2,6-diethylphenylacetic acid, 2,6-diethyl-4-(4-methylphenyl)phenylacetic acid, 2,6-diethyl-4-ethynylphenylacetic acid, 2,6-diethyl-4-nitrophenylacetic acid, 2-cyano-4,6-dimethylphenylacetic acid, 2-cyano-6-ethyl-4-methylphenylacetic acid, 2,4-dichloro-6-methylphenylacetic acid, 2-chloro-4,6-dimethylphenylacetic acid, 2-chloro-6-ethyl-4-methylphenylacetic acid, 2,4-dichloro-6-ethylphenylacetic acid, 2-bromo-6-ethyl-4-methylphenylacetic acid, 4-chloro-2-ethyl-6-methoxyphenylacetic acid, 2-ethyl-6-methoxy-4-methylphenylacetic acid, 2-ethyl-6-ethynyl-4-phenylphenylacetic acid, 2-chloro-6-ethyl-4-phenylphenylacetic acid, 2-ethyl-6-methoxy-4-phenylphenylacetic acid, 2,6-diethyl-4-trifluoromethylphenylacetic acid, 2,6-diethyl-4-trifluoromethoxyphenylacetic acid, 2-ethyl-6-ethynyl-4-methylphenylacetic acid, 2-chloro-6-ethyl-4-methoxyphenylacetic acid, 2-cyclopropyl-6-ethyl-4-methylphenylacetic acid, 4-cyclopropyl-2,6-diethylphenylacetic acid, 5-(4-chlorophenyl)-2-methylphenylacetic acid, 5-(4-fluorophenyl)-2-methylphenylacetic acid, 2-bromo-4,6-dimethylphenylacetic acid, 2-methoxy-4,6-dimethylphenylacetic acid, and 2-ethynyl-4,6-dimethylphenylacetic acid.

Reference Production Process 9

The compound represented by formula (XI) can be produced, for example, in accordance with the following Reaction Scheme.

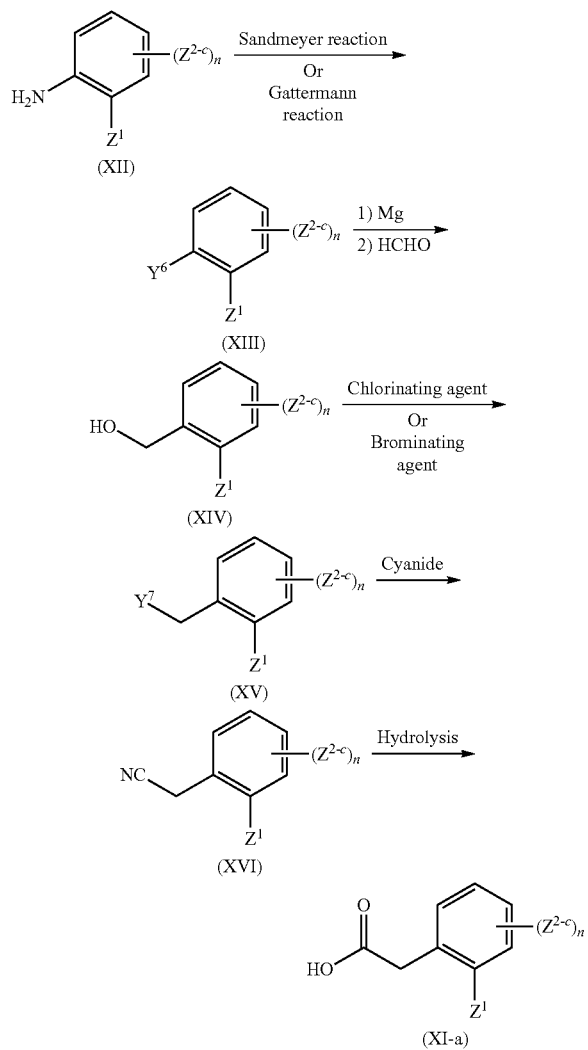

wherein $Z^1$ and n are as defined above, $Z^{2-c}$ is as defined above for $Z^2$ provided that halogen, a $C_{6-10}$ aryl group substituted by halogen, a 5- or 6-membered heteroaryl group substituted by halogen and a cyano group are excluded, $Y^6$ represents chlorine, bromine or iodine, and $Y^7$ represents chlorine or bromine.

Reference Production Process 10

The compound represented by formula (XV-a) can be produced, for example, by the following process.

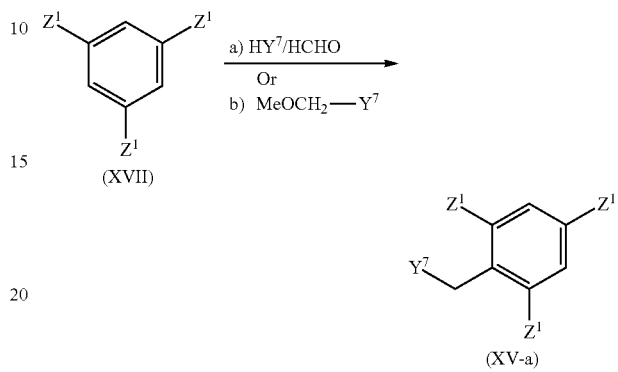

wherein $Z^1$ and $Y^7$ are as defined above.

EXAMPLES

The present invention will be described specifically by way of Examples, Reference Examples, Formulation Examples and Test Examples, however the present invention is not limited to the example.

Example 1

To a mixture of 0.30 g of 4-(2,6-diethyl-4-methylphenyl)-5-hydroxy-2,6-dimethyl-3(2H)-pyridazinone [compound (II-1-2)] and 10 mL of dichloromethane, 0.21 g of triethylamine, 0.15 g of chloromethyl ethyl ether and 0.013 g of 4-dimethylaminopyridine were added. This mixture was stirred at room temperature for 23.5 hours. The reaction mixture was concentrated under reduced pressure. To the residue, 20 mL of ice water was added, followed by extraction with ethyl acetate (20 mL×2). The organic layer was washed with an aqueous saturated sodium chloride solution (10 mL×2), dried over anhydrous magnesium sulfate, and then concentrated under reduced pressure. The residue was subjected to silica gel column chromatography (ethyl acetate:hexane=1:4) to obtain 0.29 g of a solid. The solid was washed with hexane and dried to obtain 0.26 g of 4-(2,6-diethyl-4-methylphenyl)-5-ethoxymethoxy-2,6-dimethyl-3(2H)-pyridazinone [compound (I-1-2)] as white powder.

$^1$H NMR (CDCl$_3$) δ ppm: 1.12 (3H, t, J=7.1 Hz), 1.13 (6H, t, J=7.6 Hz), 2.27-2.51 (4H, m), 2.33 (3H, s), 2.34 (3H, s), 3.51 (2H, q, J=7.1 Hz), 3.74 (3H, s), 4.53 (2H, s), 6.95 (2H, s).

The compounds of the present invention produced in the same manner as Example 1 are shown in Table 1.

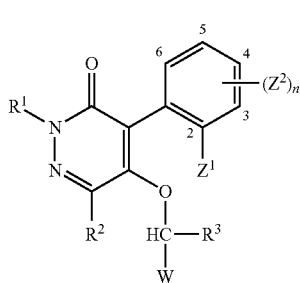

(I)

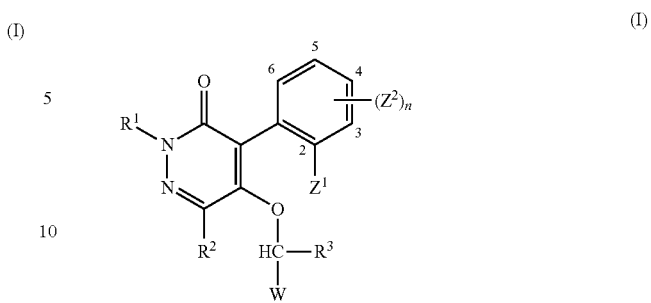

(I)

TABLE 1

| No. | $R^1$ | $R^2$ | $Z^1$ | $(Z^2)_n$ | $R^3$ | W | Melting point/° C. |
|---|---|---|---|---|---|---|---|
| I-1-1 | Me | Me | Et | 4-Me, 6-Et | H | OMe | 79-80 |
| I-1-2 | Me | Me | Et | 4-Me, 6-Et | H | OEt | 71-72 |
| I-1-3 | Me | Me | Et | 4-Et, 6-Et | H | OEt | 94-95 |
| I-1-4 | Me | Me | Et | 4-Me, 6-Me | H | OEt | 40-42 |
| I-1-5 | Me | Me | Et | 4-Et, 6-Et | H | OCH$_2$Ph | 78-80 |
| I-1-6 | Me | Me | Me | 5-(4-Cl—Ph) | H | OMe | 120-122 |
| I-1-7 | Me | H | Me | 4-Me, 6-Me | H | OMe | 101-102 |
| I-1-8 | Me | H | Me | 4-Me, 6-Me | H | OEt | * |

Regarding the compound with asterisk (*) in the column of melting point in Table 1, $^1$H NMR data are shown below.

Compound (I-1-8):

$^1$H NMR (CDCl$_3$) δ ppm: 1.19 (3H, t, J=6.5 Hz), 2.04 (6H, s), 2.30 (3H, s), 3.62 (2H, q, J=6.5 Hz), 3.82 (3H, s), 5.13 (2H, s), 6.92 (2H, s), 8.03 (1H, s).

Example 2

Under a nitrogen atmosphere, to a mixture of 0.10 g of sodium hydride (60% in oil) and 5 mL of N,N-dimethylformamide, a solution of 0.30 g of 4-(2,6-diethyl-4-methylphenyl)-5-hydroxy-2,6-dimethyl-3(2H)-pyridazinone [compound (II-1-2)] in 5 mL of N,N-dimethylformamide was added dropwise under ice cooling. This mixture was stirred at room temperature for 20 minutes. To the reaction mixture, a solution of 0.19 g of chloromethyl methyl sulfide in 3 mL of N,N-dimethylformamide was added dropwise. Next, this mixture was stirred at room temperature for 22 hours. To the reaction mixture, 30 mL of ice water was added, followed by extraction with ethyl acetate (20 mL×2). The organic layer was washed with water (20 mL×2), dried over anhydrous magnesium sulfate and then concentrated under reduced pressure. The residue was subjected to silica gel column chromatography (ethyl acetate:hexane=1:4) to obtain 0.16 g of a solid. The solid was washed with hexane and dried to obtain 0.15 g of 4-(2,6-diethyl-4-methylphenyl)-2,6-dimethyl-5-methylthiomethoxy-3(2H)-pyridazinone [compound (I-2-1)] as white powder.

$^1$H NMR (CDCl$_3$), δ ppm: 1.13 (6H, t, J=7.6 Hz), 2.10 (3H, s), 2.30-2.50 (4H, m), 2.34 (6H, s), 3.75 (3H, s), 4.51 (2H, s), 6.97 (2H, s).

The compounds of the present invention produced in the same manner as Example 2 are shown in Table 2.

TABLE 2

| No. | $R^1$ | $R^2$ | $Z^1$ | $(Z^2)_n$ | $R^3$ | W | Melting point/° C. |
|---|---|---|---|---|---|---|---|
| I-2-1 | Me | Me | Et | 4-Me, 6-Et | H | SMe | 102-103 |
| I-2-2 | Me | Me | Et | 4-Et, 6-Et | H | SMe | 88-89 |
| I-2-3 | Me | Me | Me | 5-(4-Cl—Ph) | H | SMe | * |

Regarding the compound with asterisk (*) in the column of melting point in Table 2, $^1$H NMR data are shown below.

Compound (I-2-3):

$^1$H NMR (CDCl$_3$) δ ppm: 2.06 (3H, s), 2.26 (3H, s), 2.37 (3H, s), 3.78 (3H, s), 4.59 (2H, s), 7.32-7.62 (7H, m).

Example 3

To a mixture of 0.30 g of 2,6-dimethyl-5-methylthiomethoxy-4-(2,4,6-triethylphenyl)-3(2H)-pyridazinone [compound (I-2-2)] and 4 mL of dichloromethane, 77 mg of m-chloroperbenzoic acid was added, followed by stirring at room temperature for 30 minutes. To the reaction mixture, an aqueous saturated sodium thiosulfate solution (10 mL) was added, followed by extraction with chloroform (10 mL×2). The organic layers was washed with an aqueous saturated sodium bicarbonate solution (10 mL), dried over anhydrous magnesium sulfate and then concentrated under reduced pressure. The residue was subjected to silica gel column chromatography (ethyl acetate) to obtain 0.16 g of 2,6-dimethyl-5-methylsulfinylmethoxy-4-(2,4,6-triethylphenyl)-3 (2H)-pyridazinone [compound (I-3-1)].

$^1$H NMR (CDCl$_3$) δ ppm: 1.14 (6H, t, J=7.6 Hz), 1.25 (3H, t, J=8.0 Hz), 2.08 (3H, s), 2.34 (3H, s), 2.32-2.49 (4H, m), 2.64 (2H, q, J=7.6 Hz), 3.75 (3H, s), 4.49 (2H, s), 6.98 (2H, s).

Example 4

To a mixture of 0.30 g of 2,6-dimethyl-5-methylthiomethoxy-4-(2,4,6-triethylphenyl)-3(2H)-pyridazinone [compound (I-2-2)] and 4 mL Of dichloromethane, 205 mg of m-chloroperbenzoic acid was added, followed by stirring at room temperature for 16 hours. To the reaction mixture, an aqueous saturated sodium thiosulfate solution (10 mL) was added, followed by extraction with chloroform (10 mL×2). The organic layer was washed with an aqueous saturated sodium bicarbonate solution (10 mL), dried over anhydrous magnesium sulfate and concentrated under reduced pressure. The residue was subjected to silica gel column chromatography (ethyl acetate:hexane=1:1) to obtain 0.23 g of 2,6-dimethyl-5-methylsulfonylmethoxy-4-(2,4,6-triethylphenyl)-3 (2H)-pyridazinone [compound (I-4-1)]. Melting point: 142 to 143° C.

Example 5

To a mixture of 0.31 g of 2,6-dimethyl-5-methylthiomethoxy-4-(2,4,6-triethylphenyl)-3(2H)-pyridazinone [compound (I-2-2)] and 3 mL of chloroform, 0.08 mL of sulfuryl chloride was added, followed by stirring under ice cooling for 2.5 hours. The reaction mixture was concentrated under reduced pressure. The residue was subjected to silica gel column chromatography (ethyl acetate:hexane=1:4) to obtain 0.14 g of 5-chloromethoxy-2,6-dimethyl-4-(2,4,6-triethylphenyl)-3(2H)-pyridazinone [compound (I-5-1)]. Melting point: 103 to 104° C.

Example 6

To a mixture of 0.30 g of 4-(2,6-diethyl-4-methylphenyl)-5-hydroxy-2,6-dimethyl-3(2H)-pyridazinone [compound (II-1-2)] and 5 mL of chloroform, 0.22 mL of triethylamine and 0.52 mL of ethyl N-chloromethyl-N-phenylcarbamate were added, followed by stirring at room temperature for 13.5 hours. The reaction mixture was concentrated under reduced pressure. The residue was subjected to silica gel column chromatography (ethyl acetate:hexane=1:1) to obtain 0.27 g of 4-(2,6-diethyl-4-methylphenyl)-5-(N-ethoxycarbonyl-N-phenylaminomethoxy)-2,6-dimethyl-3(2H)-pyridazinone [compound (I-6-1)].

$^1$H NMR (CDCl$_3$) δ ppm: 1.11 (6H, t, J=7.2 Hz), 1.18 (3H, t, J=7.2 Hz), 2.29 (3H, s), 2.32 (3H, s), 2.31-2.48 (4H, m), 3.73 (3H, s), 4.15 (2H, q, J=7.2 Hz), 4.80 (2H, s), 6.92 (2H, s), 7.12 (2H, d, J=7.6 Hz), 7.22-7.40 (3H, m).

Reference Example 1

To 13 mL of a solution (1 mol/L) of potassium tert-butoxide in tetrahydrofuran, a solution of 1.9 g of ethyl 2-[2-(2,6-diethyl-4-methylphenylacetyl)-2-methylhydrazono]propanoate [compound (VI-2)] in 55 mL of toluene was added dropwise over about 1 hour under a nitrogen atmosphere. This mixture was stirred at room temperature for 30 minutes. Then, the reaction mixture was concentrated under reduced pressure. To the residue, 30 mL of ice water was added, followed by washing with tert-butyl methyl ether (20 mL×2). To the aqueous layer, 1.6 g of 35% hydrochloric acid was added, followed by extraction with ethyl acetate (20 mL×3). The organic layer was washed with an aqueous saturated sodium chloride solution (20 mL×2), dried over anhydrous magnesium sulfate and then concentrated under reduced pressure. The residue was subjected to silica gel column chromatography (ethyl acetate:hexane=1:3) to obtain 0.76 g of a solid. The solid was washed with hexane and dried to obtain 0.59 g of 4-(2,6-diethyl-4-methylphenyl)-5-hydroxy-2,6-dimethyl-3(2H)-pyridazinone [compound (II-1-2)] as white powder.

The compounds produced in the same manner as Reference Example 1 are shown in Table 3.

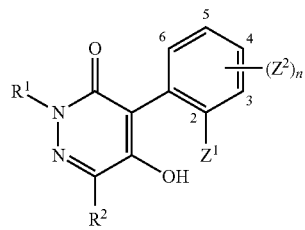

(II)

TABLE 3

| Compound | R$^1$ | R$^2$ | Z$^1$ | (Z$^2$)$_n$ | Melting point/° C. |
|---|---|---|---|---|---|
| II-1-1 | Me | Me | Me | 4-Me, 6-Me | 199-201 |
| II-1-2 | Me | Me | Et | 4-Me, 6-Et | 205-206 |
| II-1-3 | Me | Me | Et | 4-Et, 6-Et | 188-190 |
| II-1-4 | Me | Me | Et | 4-Me, 6-Me | 176-177 |

Reference Example 2

To a mixture of 0.55 g of potassium tert-butoxide and 20 mL of tetrahydrofuran, a solution of 0.79 g of ethyl 2-[2-(4-chloro-2,6-diethylphenylacetyl)-2-methylhydrazono]propanoate [compound (VI-7)] in toluene (15 mL) was added dropwise at 36 to 38° C. over about 20 minutes under a nitrogen atmosphere. This mixture was stirred at 36 to 38° C. for 10 minutes. The reaction mixture was concentrated under reduced pressure. To the residue, 20 mL of ice water was added, followed by washing with tert-butyl methyl ether (20 mL×2). To the aqueous layer, 0.6 g of 35% hydrochloric acid was added, followed by extraction with ethyl acetate (20 mL×2). The organic layer was washed with an aqueous saturated sodium chloride solution (20 mL×2), dried over anhydrous magnesium sulfate and then concentrated under reduced pressure. The resultant residue was subjected to silica gel column chromatography (ethyl acetate:hexane=1:4) to obtain 0.1 g of a solid. The solid was washed with an ethyl acetate-hexane mixed solution (1:10) and dried to obtain 0.07 g of 4-(4-chloro-2,6-diethylphenyl)-5-hydroxy-2,6-dimethyl-3(2H)-pyridazinone [compound (II-1-5)] as white powder.

The compounds produced in the same manner as Reference Example 2 are shown in Table 4.

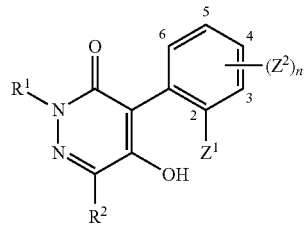

(II)

TABLE 4

| No. | R¹ | R² | Z¹ | (Z²)ₙ | Melting point/° C. |
|---|---|---|---|---|---|
| II-1-5 | Me | Me | Et | 4-Cl, 6-Et | 234-235 |
| II-1-6 | Me | Me | Me | 5-(4-Cl—Ph) | 234-236 |

Reference Example 3

To a mixture of 55 ml of dioxane and 17 ml of water were added 1.38 g of 4-chloro-5-methoxy-2-methyl-3(2H)-pyridazinone, 1.55 g of 2,4,6-trimethylphenylboronic acid, 1.86 g of sodium carbonate, 2.53 g of tetrabutylammonium bromide and 0.38 g of tetrakis(triphenylphosphine)palladium. This mixture was heated under reflux for 32 hours under a nitrogen atmosphere. A part of the reaction mixture was evaporated. To the resultant concentrate, 150 ml of water was added, followed by extraction with ethyl acetate (twice). The organic layer was washed with an aqueous sodium chloride solution, dried over anhydrous magnesium sulfate and then concentrated under reduced pressure. The residue was subjected to silica gel column chromatography (ethyl acetate: hexane=1:2) to obtain 0.77 g of 5-methoxy-2-methyl-4-(2,4,6-trimethylphenyl)-3(2H)-pyridazinone [compound (V-2-1)] as a white crystal. Melting point: 186 to 192° C.

To a solution of 1.4 g of the compound (V-2-1) in 7 ml of acetic acid was added 5 ml of 47% hydrobromic acid, followed by stirring at 80° C. for 5.5 hours and then at 100° C. for 14.5 hours. The reaction mixture was concentrated until reduced by half. To the residue, cold water was added to form a crystal. The crystal was collected by filtration, washed with water and then dried. The crystal was washed with an ethyl acetate-hexane mixed solution (2:1) and dried to obtain 1.1 g of 5-hydroxy-2-methyl-4-(2,4,6-trimethylphenyl)-3(2H)-pyridazinone [compound (II-2-1)] as a white crystal.

Melting point: 272-275° C.

¹H NMR (CDCl₃) δ ppm: 2.04 (6H, s), 2.29 (3H, s), 3.89 (3H, s), 6.97 (2H, s), 7.67 (1H, s).

Among the compounds represented by formula (II), the following one was produced by the manner similar to Reference Example 3.

5-Hydroxy-2-methyl-4-(2,4,6-triethylphenyl)-3(2H)-pyridazinone [compound (II-2-2)] mp: 212-214° C.

Reference Example 4

To a mixture of 2.0 g of ethyl 2-(methylhydrazono)propanoate and 35 mL of acetonitrile, 1.5 g of potassium carbonate was added. To the mixture, a solution of 2.6 g of 2,6-diethyl-4-methylphenylacetyl chloride in 10 mL of acetonitrile was added dropwise over about 20 minutes under ice cooling. This mixture was stirred at room temperature for 3.5 hours. The reaction mixture was concentrated under reduced pressure. To the residue, 20 mL of ice water was added, followed by extraction with ethyl acetate (20 mL×3). The organic layer was washed with an aqueous saturated sodium chloride solution (20 mL×2), dried over anhydrous magnesium sulfate and concentrated under reduced pressure. The residue was subjected to basic alumina column chromatography (ethyl acetate:hexane=1:3) to obtain 1.9 g of ethyl 2-[2-(2,6-diethyl-4-methylphenylacetyl)-2-methylhydrazono]propanoate [compound (VI-2)] as a white crystal.

The compounds represented by formula (VI) produced in the same manner as Reference Example 4 are shown in Table 5.

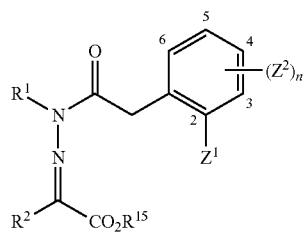

(VI)

TABLE 5

| No. | R¹ | R² | Z¹ | (Z²)ₙ | R¹⁵ | Melting point/° C. |
|---|---|---|---|---|---|---|
| VI-1 | Me | Me | Me | 4-Me, 6-Me | Et | 90-91 |
| VI-2 | Me | Me | Et | 4-Me, 6-Et | Et | 73-76 |
| VI-3 | Me | Me | Et | 4-Et, 6-Et | Et | 63-66 |
| VI-4 | Me | Me | Et | 4-Me, 6-Me | Et | * |
| VI-5 | Me | Me | Me | 4-Me, 6-Me | Me | * |
| VI-6 | Me | Me | Et | 4-Et, 6-Et | Me | * |

Regarding the compounds with asterisk (*) in the column of melting point in Table 5, ¹H NMR data are shown below.

Compound (VI-4):

¹H NMR (CDCl₃) δ ppm: 1.16 (3H, t, J=7.7 Hz), 1.36 (3H, t, J=7.2 Hz), 2.22 (3H, s), 2.27 (3H, s), 2.30 (3H, br.s), 2.56 (2H, q, J=7.7 Hz), 3.39 (3H, br.s), 4.02 (2H, br.s), 4.32 (2H, q, J=7.1 Hz), 6.86 (2H, br.s).

Compound (VI-5):

¹H NMR (CDCl₃) δ ppm: 2.21 (6H, s), 2.25 (3H, s), 2.29 (3H, br.s), 3.39 (3H, br.s), 3.88 (3H, s), 3.99 (2H, br.s), 6.85 (2H, s).

Compound (VI-6):

¹H NMR (CDCl₃) δ ppm: 1.18 (6H, t, J=7.6 Hz), 1.23 (3H, t, J=7.6 Hz), 2.32 (3H, br.s), 2.57 (4H, q, J=7.6 Hz), 2.60 (2H, q, J=7.6 Hz), 3.40 (3H, br.s), 3.88 (3H, s), 4.04 (2H, br.s), 6.90 (2H, s).

Reference Example 5

To a mixture of 1.1 g of ethyl 2-(methylhydrazono)propanoate and 20 mL of acetonitrile, 0.68 g of potassium carbonate was added. To this mixture, a solution of 1.26 g of 4-chloro-2,6-diethylphenylacetyl chloride in 8 mL of acetonitrile was added dropwise over about 10 minutes under ice cooling. This mixture was stirred at room temperature for 3 hours. The reaction mixture was concentrated under reduced pressure. To the residue, 20 mL of ice water was added, followed by extraction with ethyl acetate (20 mL, 10 mL×2). The organic layer was washed with an aqueous saturated sodium chloride solution (20 mL×2), dried over anhydrous magnesium sulfate and concentrated under reduced pressure. The residue was subjected to basic alumina column chromatography (ethyl acetate:hexane=1:6) to obtain 1.2 g of a pale yellow solid. The solid was washed with hexane and then dried to obtain 0.79 g of ethyl 2-[2-(4-chloro-2,6-diethylphenylacetyl)-2-methylhydrazono]propanoate [compound (VI-7)] as white powder.

The compound represented by formula (VI) produced in the same manner as Reference Example 5 are shown in Table 6. Compound represented by formula (VI):

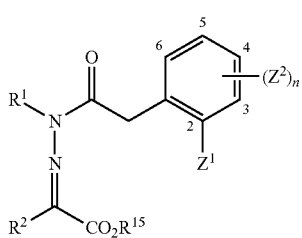

(VI)

TABLE 6

| No. | R¹ | R² | Z¹ | (Z²)ₙ | R¹⁵ | Melting point/ °C. |
|---|---|---|---|---|---|---|
| VI-7 | Me | Me | Et | 4-Cl, 6-Et | Et | 85-89 |
| VI-8 | Me | Me | Me | 5-(4-Cl—Ph) | Et | * |

Regarding the compound with asterisk (*) in the column of melting point in Table 6, ¹H NMR data are shown below.

Compound (VI-8):

¹H NMR (CDCl₃) δ ppm: 1.33 (3H, t, J=7.2 Hz), 2.21 (3H, s), 2.35 (3H, s), 3.37 (3H, s), 4.06 (2H, br.s), 4.28 (2H, q, J=7.1 Hz), 7.22 (1H, d, J=7.8 Hz), 7.30-7.40 (3H, m), 7.43 (1H, br.s), 7.47 (2H, d, J=8.3 Hz).

Reference Example 6

To a mixture of 283.03 g of 2,6-diethyl-4-methylphenylacetic acid and 690.8 g of toluene, 120.81 g of thionyl chloride was added dropwise at 100° C. over 3 hours. This mixture was stirred at 100° C. for 3.5 hours. The reaction mixture was cooled to room temperature and then concentrated under reduced pressure to obtain 274.8 g of a brown oil. This brown oil was distilled to obtain 2,6-diethyl-4-methylphenylacetyl chloride as a yellow oil. Boiling point: 116 to 120° C. (0.20 kPa).

¹H NMR (CDCl₃) δ ppm: 1.20 (6H, t, J=7.6 Hz), 2.31 (3H, s), 2.59 (4H, q, J=7.6 Hz), 4.24 (2H, s), 6.91 (2H, s).

In accordance with Reference Example 6, the following compound was produced.

2,4,6-Triethylphenylacetyl chloride:

¹H NMR (CDCl₃) δ ppm: 1.21 (6H, t, J=7.6 Hz), 1.23 (3H, t, J=7.6 Hz), 2.60 (4H, q, J=7.6 Hz), 2.61 (2H, q, J=7.6 Hz), 4.25 (2H, s), 6.94 (2H, s).

Reference Example 7

A mixture of 236.77 g of 2,6-diethyl-4-methylphenylacetonitrile (GC-area: 71%) and 713.5 g of 65% sulfuric acid was stirred at 130° C. for 25 hours. This mixture was cooled to room temperature, and thereto were added 760 g of toluene and 900 g of water. The mixture was separated. The organic layer was washed with 710 mL of water. After drying over anhydrous magnesium sulfate, the solvent was distilled off to obtain 283.58 g of a brown crystal containing 2,6-diethyl-4-methylphenylacetic acid.

¹H NMR (CDCl₃) δ ppm: 1.19 (6H, t, J=7.6 Hz), 2.29 (3H, s), 2.61 (4H, q, J=7.6 Hz), 3.72 (2H, s), 6.89 (2H, s), 10-11 (1H, br.).

In accordance with Reference Example 7, the following compound was produced.

2,4,6-Triethylphenylacetic acid:

¹H NMR (CDCl₃) δ ppm: 1.20 (6H, t, J=7.6 Hz), 1.23 (3H, t, J=7.6 Hz), 2.60 (2H, q, J=7.6 Hz), 2.63 (4H, q, J=7.6 Hz), 3.73 (2H, s), 6.92 (2H, s), 10-12 (1H, br.).

Reference Example 8

In a mixture of 50 g of water and 99 g of acetonitrile was dissolved 27.98 g of sodium cyanide. To this mixture, a solution of 157.18 g of 2,6-diethyl-4-methylbenzyl chloride (GC-area: 71%) in acetonitrile (293 g) was added dropwise at 75° C. over 2.5 hours. This mixture was stirred at 75° C. for 3 hours. To the reaction mixture was added 99 g of water, and the mixture was separated. The organic layer was concentrated. To the residue were added 99 g of water and 198 g of hexane and the mixture was separated. The organic layer was washed with 99 g of an aqueous saturated sodium chloride solution, dried over anhydrous magnesium sulfate and then concentrated to obtain 123.46 g of 2,6-diethyl-4-methylphenylacetonitrile (GC-area: 71%) as a brown oil.

¹H NMR (CDCl₃) δ ppm: 1.26 (6H, t, J=7.6 Hz), 2.31 (3H, s), 2.68 (4H, q, J=7.6 Hz), 3.64 (2H, s), 6.92 (2H, s).

In accordance with Reference Example 8, the following compound was produced.

2,4,6-Triethylphenylacetonitrile:

¹H NMR (CDCl₃) δ ppm: 1.23 (3H, t, J=7.7 Hz), 1.27 (6H, t, J=7.7 Hz), 2.61 (2H, q, J=7.7 Hz), 2.70 (4H, J=7.7 Hz), 3.65 (2H, s), 6.94 (2H, s).

Reference Example 9

To a mixture of 138.41 g of 2,6-diethyl-4-methylbenzyl alcohol and 820 g of toluene was added dropwise 60.96 g of thionyl chloride at 25° C. over 4.5 hours. The resultant mixture was stirred for 15 hours. The reaction mixture was concentrated to obtain 159.58 g of 2,6-diethyl-4-methylbenzyl chloride (GC-area: 71%) as a brown oil.

¹H NMR (CDCl₃) δ ppm: 1.26 (6H, t, J=7.6 Hz), 2.30 (3H, s), 2.74 (4H, q, J=7.6 Hz), 4.68 (2H, s), 6.89 (2H, s).

In accordance with Reference Example 9, the following compound was produced.

2,4,6-Triethylbenzyl chloride:

¹H NMR (CDCl₃) δ ppm: 1.23 (3H, t, J=7.6 Hz), 1.28 (6H, t, J=7.6 Hz), 2.61 (2H, q, J=7.6 Hz), 2.77 (4H, q, J=7.6 Hz), 4.70 (2H, s), 6.93 (2H, s).

Reference Example 10

Under a nitrogen atmosphere, 11.24 g of magnesium, 200 g of tetrahydrofuran, 0.1 g of iodine and 1.0 g of 1,2-dibromoethane were mixed. This mixture was heated to 60° C. To this mixture, a small amount of 2,6-diethyl-4-methylbromobenzene was added. To this mixture, 0.1 g of iodine and 1.0 g of 1,2-dibromoethane were added. Then, 2,6-diethyl-4-methylbromobenzene (the total amount including the amount added first: 100.12 g) was added dropwise over 2.5 hours. After completion of addition, the resultant mixture was stirred at 50° C. for 1.5 hours. This mixture was cooled to 30° C. To this mixture, 14.84 g of paraformaldehyde was added portionwise in five additions over 30 minutes. The resultant mixture was stirred at 30° C. for 2 hours. To the reaction mixture, 143 g of 10% hydrochloric acid was added, followed by extraction with 300 g of tert-butyl methyl ether. The organic layer was dried over anhydrous magnesium sulfate and then concentrated to obtain 77.56 g of 2,6-diethyl-4-methylbenzyl alcohol as a yellow crystal.

¹H NMR (CDCl₃) δ ppm: 1.24 (6H, t, J=7.6 Hz), 1.32 (1H, s), 2.30 (3H, s), 2.74 (4H, q, J=7.6 Hz), 4.70 (2H, s), 6.90 (2H, s).

In accordance with Reference Example 10, the following compound was produced.

2,4,6-Triethylbenzyl alcohol:

¹H NMR (CDCl₃) δ ppm: 1.23 (3H, t, J=7.7 Hz), 1.25 (6H, t, J=7.7 Hz), 1.59 (1H, br.s), 2.60 (2H, q, J=7.7 Hz), 2.77 (4H, q, J=7.7 Hz), 4.73 (2H, s), 6.93 (2H, s).

Reference Example 11

To a mixture of 3.00 g of 1,3,5-triethylbenzene (purity: 93%) and 5.58 g of acetic acid, 0.82 g of paraformaldehyde and 4.7 mL of a 33% solution of hydrogen bromide in acetic acid were added. This mixture was heated at 45° C. for 7.5 hours under stirring. After the reaction mixture was cooled to room temperature, 16.8 g of water and 16.8 g of toluene were added thereto. The reaction mixture was separated. The organic layer was washed sequentially with 11.2 g of water, a mixture of 5.6 g of an aqueous saturated sodium hydrogen carbonate solution and 5.6 g of water, and 11.2 g of water, dried over anhydrous magnesium sulfate, and then concentrated to obtain 4.72 g of 2,4,6-triethylbenzyl bromide (GC-area: 84%) as a yellow oil.

¹H NMR (CDCl₃) δ ppm: 1.23 (3H, t, J=7.6 Hz), 1.29 (6H, t, J=7.6 Hz), 2.60 (2H, q, J=7.6 Hz), 2.76 (4H, q, J=7.6 Hz), 4.62 (2H, s), 6.91 (2H, s).

Reference Example 12

A mixture of 81.1 g of 1,3,5-triethylbenzene, 60.4 g of chloromethyl methyl ether and 6.0 g of acetic acid was stirred in a sealed tube at 120° C. for 7 hours. The reaction mixture was poured into 500 ml of water and extracted with hexane. The organic layer was washed with an aqueous sodium bicarbonate solution, dried over anhydrous magnesium sulfate and then concentrated. The residue was distilled under reduced pressure to obtain 68.07 g of 2,4,6-triethylbenzyl chloride. Boiling point: 88 to 98° C. (0.18 kPa).

Formulation Examples will be shown below.

Formulation Example 1

| Wettable powder | |
| --- | --- |
| Compound (I-1-2) | 50% by weight |
| Sodium lignin sulfonate | 5% by weight |
| Polyoxyethylene alkyl ether | 5% by weight |
| White carbon | 5% by weight |
| Clay | 35% by weight |

The above ingredients are mixed and ground to obtain a wettable powder.

In the same manner, each of the compounds (I-1-1), (I-1-3) to (I-1-8), (I-2-1) to (I-2-3), (I-3-1), (I-4-1), (I-5-1) and (I-6-1) is used instead of the compound (I-1-2) to obtain a wettable powder of each compound.

Formulation Example 2

| Granule | |
| --- | --- |
| Compound (I-1-3) | 1.5% by weight |
| Sodium lignin sulfonate | 2% by weight |
| Talc | 40% by weight |
| Bentonite | 56.5% by weight |

The above ingredients are mixed, kneaded with water, and then granulated to obtain a granule.

In the same manner, each of the compounds (I-1-1), (I-1-2), (I-1-4) to (I-1-8), (I-2-1) to (I-2-3), (I-3-1), (I-4-1), (I-5-1) and (I-6-1) is used instead of the compound (I-1-3) to obtain a granule of each compound.

Formulation Example 3

| Flowable formulation | |
| --- | --- |
| Compound (I-1-4) | 10% by weight |
| White carbon containing 50% by weight of polyoxyethylene alkyl ether sulfate ammonium salt | 35% by weight |
| Water | 55% by weight |

The above ingredients are mixed and finely ground by a wet grinding method to obtain a flowable formulation.

In the same manner, each of the compounds (I-1-1) to (I-1-3), (I-1-5) to (I-1-8), (I-2-1) to (I-2-3), (I-3-1), (I-4-1), (I-5-1) and (I-6-1) is used instead of the compound (I-1-4) to obtain a flowable formulation of each compound.

Test Example 1-1

A plastic cup with a diameter of 8 cm and a depth of 6.5 cm was filled with soil. Seeds of *Lolium multiflorum* were sowed in the cup, and then the plant was grown until the first to second leaf stage. Then, a determined amount of a test solution containing the compound of the present invention was sprayed onto the whole plant uniformly. The test solution was prepared by dissolving a predetermined amount of the compound of the present invention in a 2% solution of Tween 20 (polyoxyethylene sorbitan fatty acid ester, MP Biomedicals, Inc.) in dimethylformamide and then, diluting the solution with water. After the spray treatment, the plant was grown in a greenhouse. After 20 days, a controlling effect of the compound on *Lolium multiflorum* was visually evaluated. The effect was classified into 11 levels, from 0 to 10 (0 represents "no effect"; 10 represents "complete death"; and a state of the plant therebetween is classified into 1 to 9).

Compound D as shown below was similarly tested as a comparative example.

Comparative Example (Compound D)

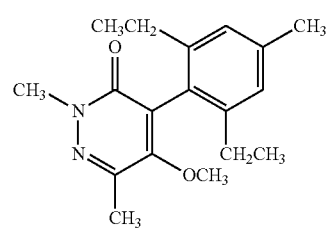

As a result, the compounds (I-1-1), (I-1-2), (I-1-3), (I-1-4), (I-2-1) and (I-6-1) showed an effect of 8 or more at a treatment amount of 250 g/ha. In contrast, Compound D showed an effect of 0 at a treatment amount of 250 g/ha.

Test Example 1-2

A plastic cup with a diameter of 8 cm and a depth of 6.5 cm was filled with soil. Seeds of *Echinochloa crus-galli* were sowed in the cup, and then the plant was grown until the second- to third-leaf stage. Then, a determined amount of a test solution containing the compound of the present invention was sprayed onto the whole plant uniformly. The test solution was prepared by dissolving a predetermined amount of the compound of the present invention in a 2% solution of Tween 20 (polyoxyethylene sorbitan fatty acid ester, MP Biomedicals, Inc.) in dimethylformamide and then diluting the solution with water. After the spray treatment, the plant was grown in a greenhouse. After 20 days, a controlling effect of the compound on *Echinochloa crus-galli* was visually evaluated. The effect was classified into 11 levels, from 0 to 10 (0 represents "no effect"; 10 represents "complete death"; and a state of the plant therebetween is classified into 1 to 9).

Compound D was similarly tested as a comparative example.

As a result, the compounds (I-1-1), (I-1-2), (I-1-3), (I-1-4), (I-1-5), (I-1-6), (I-1-8), (I-2-1), (I-2-2), (I-2-3), (I-3-1), (I-5-1) and (I-6-1) showed an effect of 8 or more at a treatment amount of 1,000 g/ha. In contrast, Compound D showed an effect of 0 at a treatment amount of 1,000 g/ha.

Test Example 1-3

A plastic cup with a diameter of 8 cm and a depth of 6.5 cm was filled with soil. Seeds of *Galium aparine* were sowed in the cup, and then the plant was grown until the second- to third-leaf stage. Then, a determined amount of a test solution containing the compound of the present invention was sprayed onto the whole plant uniformly. The test solution was prepared by dissolving a predetermined amount of the compound of the present invention in a 2% solution of Tween 20 (polyoxyethylene sorbitan fatty acid ester, MP Biomedicals, Inc.) in dimethylformamide and then diluting the solution with water. After the spray treatment, the plant was grown in a greenhouse. After 20 days, a controlling effect of the compound on *Galium aparine* was visually evaluated. The effect was classified into 11 levels, from 0 to 10 (0 represents "no effect"; 10 represents "complete death"; and a state of the plant therebetween is classified into 1 to 9).

Compound D was similarly tested as a comparative example.

As a result, the compounds (I-1-1), (I-1-2), (I-1-3), (I-1-4), (I-1-5), (I-2-1), (I-2-2), (I-3-1), (I-5-1) and (I-6-1) showed an effect of 8 or more at a treatment amount of 250 g/ha. In contrast, Compound D showed an effect of 0 at a treatment amount of 250 g/ha.

Test Example 2-1

The formulation of the compound of the present invention obtained in Formulation Example 3 was diluted with water so that the concentration of the active ingredient became 500 ppm to prepare a test solution.

An artificial diet, Silkmate 2S (Nihon Nosan Kogyo Corp.) was sliced into 2 mm in thickness and then placed on the bottom of a polyethylene cup. Then, 1 mL of the test solution was poured into the polyethylene cup. After air dried, 30 first-instar larvae of *Adoxophyes orana* were released into the polyethylene cup, and the cup was sealed with a lid. After the polyethylene cup was kept at 25° C. for 7 days, the number of surviving insects was counted. A death rate was calculated by the following equation, and the effect of the tested compound was evaluated with the following insecticidal indexes.

Death rate (%)={1−(Number of surviving insects/Number of tested insects)}×100

Insecticidal indexes 4: death rate of 100%, 3: death rate of 80-99%, 2: death rate of 60-79%, 1: death rate of 30-59%, 0: death rate of 0-29%

As a result, the compound (I-1-6) was evaluated as an index of 4.

Test Example 2-2

The formulation of the compound of the present invention obtained in Formulation Example 3 was diluted with water so that the concentration of the active ingredient became 500 ppm to prepare a test solution.

An artificial diet, Insecta LF (Nihon Nosan Kogyo Corp.) was sliced into 2 mm in thickness and then placed on the bottom of a polyethylene cup. Then, 1 mL of the test solution was poured into the polyethylene cup. After air dried, 5 fourth-instar larvae of *Spodoptera litura* were released into the polyethylene cup, and the cup was sealed with a lid. After the polyethylene cup was kept at 25° C. for 6 days, the number of surviving insects was counted. A death rate was calculated by the following equation, and the effect of the tested compound was evaluated with the following insecticidal indexes.

Death rate (%)={1−(Number of surviving insects/Number of tested insects)}×100

Insecticidal indexes 4: death rate of 100%, 3: death rate of 80-99%, 2: death rate of 60-79%, 1: death rate of 30-59%, 0: death rate of 0-29%

As a result, the compound (I-1-6) was evaluated as an index of 3.

Test Example 2-3

The formulation of the compound of the present invention obtained in Reference Example 3 was diluted with water so that the concentration of the active ingredient became 500 ppm to prepare a test solution.

0.7 mL of the test solution was diluted with ion-exchanged water so that the active ingredient concentration became 3.5 ppm. Into the dilution, 20 last-instar larvae of *Culex pipiens pallens* were released. After 8 days, the number of dead insects was counted.

A death rate was calculated by the following equation, and the effect of the tested compound was evaluated with following insecticidal indexes of 4: death rate of 91-100%, 2: death rate of 11-90%, and 0: death rate of 0-10%.

Death rate (%)=(Number of dead insects/Number of tested insects)×100

As a result, the compound (I-1-6) was evaluated as an index of 4.

Test Example 2-4

The formulation of the compound of the present invention obtained in Reference Example 3 was diluted with water so that the concentration of the active ingredient became 500 ppm to prepare a test solution.

On cabbage (*Brassicae oleacea*) at the third-leaf stage planted in a polyethylene cup, 20 mL/cup of the test solution was sprayed. After the test solution was dried, the aerial part of the cabbage was cut off, and then placed in a cup (volume: 50 mL). Into the cup, 5 second-instar larvae of *Plutella xylostella*, and the cup was sealed with a lid. After the cup was kept at 25° C. for 5 days, the number of dead insects was counted. A death rate was calculated by the following equation.

Death rate (%)=(Number of dead insects/Number of tested insects)×100

As a result, each of the compounds (I-1-6) and (I-2-3) showed a death rate of 80% or more.

Test Example 2-5

The formulation of the compound of the present invention obtained in Reference Example 3 was diluted with water so that the concentration of the active ingredient became 500 ppm to prepare a test solution.

On a rice seedling at the second-leaf stage planted in a polyethylene cup, 10 mL of the test solution was sprayed. After the test solution was dried, 30 first-instar larvae of *Nilaparvata lugens* were released on the plant. The plant was kept at 25° C. for 6 days. Then, the number of the insects parasitizing the plant was counted, and a controlling value was determined by the following equation.

Controlling value (%)={1−($Cb$×$Tai$)/($Cai$×$Tb$)}×100 wherein
Cb: the number of insects in a non-treated section before treatment,
Cai: the number of insects in a non-treated section on observation,
Tb: the number of insects in a treated-section before treatment,
Tai: the number of insects in a treated section on observation.

As a result, each of the compounds (I-1-6) and (I-2-3) showed a controlling value of 90% or more.

Test Example 2-6

The formulation of the compound of the present invention obtained in Reference Example 3 was diluted with water so that the concentration of the active ingredient became 500 ppm to prepare a test solution.

On a cucumber seedling at the second true leaf stage placed in a polyethylene cup, about 30 imagoes of *Aphis gossypii* were released. One day after the release of aphids, 10 mL of the test solution was sprayed on the plant. Five days after the spraying treatment, the number of the insects parasitizing the leaves of the plant was counted, and a controlling value was determined by the following equation.

Controlling value (%)={1−($Cb$×$Tai$)/($Cai$×$Tb$)}×100 wherein
Cb: the number of insects in a non-treated section before treatment,
Cai: the number of insects in a non-treated section on observation,
Tb: the number of insects in a treated-section before treatment,
Tai: the number of insects in a treated section on observation.

As a result, the compound (I-1-6) showed a controlling value of 90% or more.

Test Example 2-7

The formulation of the compound of the present invention obtained in Reference Example 4 was diluted with water so that the concentration of the active ingredient became 500 ppm to prepare a test solution.

On a tomato seedling at the third true leaf stage placed in a polyethylene cup, imagoes of *Bemisia tabaci* were released and allowed to lay eggs for about 24 hours. The plant was placed in a greenhouse for 8 days. When larvae of *Bemisia tabaci* hatched from the eggs, 10 ml/cup of the test solution was sprayed. After the plant was kept at 25° C. for 7 days, the number of the larvae surviving on the tomato leaves was counted, and a controlling value was determined by the following equation.

Controlling value (%)={1−($Cb$×$Tai$)/($Cai$×$Tb$)}×100 wherein
Cb: the number of insects in a non-treated section before treatment,
Cai: the number of insects in a non-treated section on observation,
Tb: the number of insects in a treated-section before treatment,
Tai: the number of insects in a treated section on observation.

As a result, the compound (I-1-6) showed a controlling value of 90% or more.

Test Example 2-8

The formulation of the compound of the present invention obtained in Reference Example 3 was diluted with water so that the concentration of the active ingredient became 500 ppm to prepare a test solution.

On a cucumber seedling at the second true leaf stage planted in a polyethylene cup, 10 mL/cup of the test solution was sprayed. After the test solution was dried, the first true leadf was cut off and then placed in a polyethylene cup. Into the polyethylene cup, 20 larvae of *Frankliniella occidentalis* were released, and the cup was sealed with a lid. After the cup was kept at 25° C. for 7 days, the number of the insects surviving on the cucumber leaves was counted, and a controlling value was determined by the following equation.

Controlling value (%)={1−($Cb$×$Tai$)/($Cai$×$Tb$)}×100 wherein
Cb: the number of insects in a non-treated section before treatment,
Cai: the number of insects in a non-treated section on observation,
Tb: the number of insects in a treated-section before treatment,
Tai: the number of insects in a treated section on observation.

As a result, the compound (I-1-6) showed a controlling value of 90% or more.

Test Example 2-9

The formulation of the compound of the present invention obtained in Reference Example 3 was diluted with water so that the concentration of the active ingredient became 500 ppm to prepare a test solution.

A cucumber seedling grown at the first true leaf stage was removed from soil, and then, soil was washed away from the seedling. The root portion of the cucumber seedling was immersed in 5 ml of the test solution. One day after the treatment, 30 imagoes of *Aphis gossypii* were allowed to adhere onto the surfaces of the cucumber leaves. After 7 days, the number of the insects surviving on the cucumber leaves was counted, and a controlling value was determined by the following equation.

Controlling value (%)={1−($Cb$×$Tai$)/($Cai$×$Tb$)}×100 wherein
Cb: the number of insects in a non-treated section before treatment,
Cai: the number of insects in a non-treated section on observation,
Tb: the number of insects in a treated-section before treatment,
Tai: the number of insects in a treated section on observation.

As a result, each of the compounds (I-2-1) and (I-1-6) showed a controlling value of 90% or more.

INDUSTRIAL APPLICABILITY

The compound of the present invention has a weed-controlling effect and an arthropod-controlling effect.

The invention claimed is:

1. A pyridazinone compound represented by formula (I):

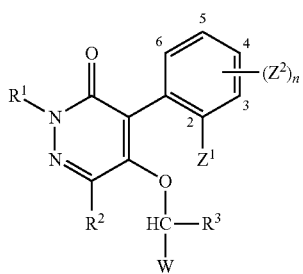

(I)

wherein:
R$^1$ represents a C$_{1-6}$ alkyl group or a (C$_{1-6}$ alkyloxy)C$_{1-6}$ alkyl group,
R$^2$ and R$^3$ are the same or different, and represent hydrogen or a C$_{1-6}$ alkyl group,
W represents halogen, or any one of the groups represented by the following formulas:

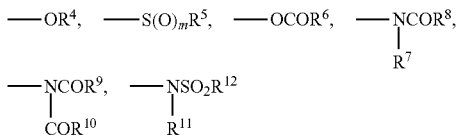

wherein R$^4$, R$^5$, R$^7$ and R$^{11}$ each represent a C$_{1-6}$ alkyl group, a C$_{3-8}$ cycloalkyl group, a C$_{3-6}$ alkenyl group, a C$_{3-6}$ alkynyl group, a C$_{6-10}$ aryl group or a (C$_{6-10}$ aryl)C$_{1-6}$ alkyl group,
R$^{12}$ represents a C$_{1-6}$ alkyl group, a C$_{3-8}$ cycloalkyl group, a C$_{3-6}$ alkenyl group, a C$_{3-6}$ alkynyl group, a C$_{6-10}$ aryl group or a (C$_{6-10}$ aryl)C$_{1-6}$ alkyl group,
R$^6$, R$^8$ and R$^9$ each represent a C$_{1-6}$ alkyl group, a C$_{3-8}$ cycloalkyl group, a C$_{2-6}$ alkenyl group, a C$_{2-6}$ alkynyl group, a C$_{6-10}$ aryl group, a (C$_{6-10}$ aryl)C$_{1-6}$ alkyl group, a C$_{1-6}$ alkyloxy group, a C$_{3-8}$ cycloalkyloxy group, a C$_{3-6}$ alkenyloxy group, a C$_{3-6}$ alkynyloxy group, a C$_{6-10}$ aryloxy group or a (C$_{6-10}$ aryl)C$_{1-6}$ alkyloxy group,
R$^{10}$ represents a C$_{1-6}$ alkyl group, a C$_{3-8}$ cycloalkyl group, a C$_{2-6}$ alkenyl group, a C$_{2-6}$ alkynyl group, a C$_{6-10}$ aryl group, a (C$_{6-10}$ aryl)C$_{1-6}$ alkyl group, a C$_{1-6}$ alkyloxy group, a C$_{3-8}$ cycloalkyloxy group, a C$_{3-6}$ alkenyloxy group, a C$_{3-6}$ alkynyloxy group, a C$_{6-10}$ aryloxy group or a (C$_{6-10}$ aryl)C$_{1-6}$ alkyloxy group,
or R$^9$ and R$^{10}$ may represent, together with the carbonyl groups to which they are attached and the nitrogen atom to which the carbonyl groups are attached, a 5- or 6-membered cyclic imide group to which a benzene ring may be fused, wherein, any group represented by R$^4$, R$^5$, R$^6$, R$^7$, R$^8$, R$^9$, R$^{10}$, R$^{11}$ or R$^{12}$ may be substituted with at least one member selected from the group consisting of halogen and C$_{1-6}$ alkyloxy groups,
the C$_{3-8}$ cycloalkyl groups, the C$_{6-10}$ aryl groups, and the aryl moieties of the (C$_{6-10}$ aryl)C$_{1-6}$ alkyl groups which are represented by R$^4$, R$^5$, R$^6$, R$^7$, R$^8$, R$^9$, R$^{10}$, R$^{11}$ or R$^{12}$ may be substituted with at least one C$_{1-6}$ alkyl group,
the C$_{3-8}$ cycloalkyloxy groups, the C$_{6-10}$ aryloxy groups, and the aryl moieties of the (C$_{6-10}$ aryl)C$_{1-6}$ alkyloxy groups which are represented by R$^6$, R$^8$, R$^9$ or R$^{10}$ may be substituted with at least one C$_{1-6}$ alkyl group, and
m represents 0, 1 or 2,
Z$^1$ represents a C$_{1-6}$ alkyl group,
Z$^2$ represents a C$_{1-6}$ alkyl group, a C$_{3-8}$ cycloalkyl group, a C$_{2-6}$ alkynyl group, a C$_{1-6}$ haloalkyl group, a C$_{6-10}$ aryl group, a 5- or 6-membered heteroaryl group, a C$_{1-6}$ alkyloxy group, a C$_{1-6}$ haloalkyloxy group, halogen, a cyano group or a nitro group,
wherein, the C$_{3-8}$ cycloalkyl group, the C$_{6-10}$ aryl group and the 5- or 6-membered heteroaryl group represented by Z$^2$ may be substituted with at least one member selected from the group consisting of halogen and C$_{1-6}$ alkyl groups, and
n represents 0, 1, 2, 3 or 4, and when n is 2, 3 or 4, each Z$^2$ is the same or different.

2. The pyridazinone compound according to claim 1, wherein n is 1, 2 or 3.

3. The pyridazinone compound according to claim 1, wherein n is 0, and Z$^1$ is a C$_{2-6}$ alkyl group.

4. The pyridazinone compound according to claim 1, wherein n is 1 or 2, and Z$^2$ is attached to the 4- and/or 6-position of the benzene ring.

5. The pyridazinone compound according to claim 1, wherein Z$^1$ is a C$_{1-3}$ alkyl group, Z$^2$ is a C$_{1-3}$ alkyl group, a C$_{3-6}$ cycloalkyl group, a C$_{2-3}$ alkynyl group, a C$_{1-3}$ alkyloxy group, halogen, a cyano group, a nitro group, or a phenyl group which may be substituted with at least one member selected from the group consisting of halogen and C$_{1-3}$ alkyl groups.

6. The pyridazinone compound according to claim 1, wherein Z$^1$ is a C$_{1-3}$ alkyl group, and Z$^2$ is a C$_{1-3}$ alkyl group.

7. The pyridazinone compound according to claim 1, wherein R$^1$ is a C$_{1-3}$ alkyl group or a (C$_{1-3}$ alkyloxy)C$_{1-3}$ alkyl group.

8. The pyridazinone compound according to claim 1, wherein R$^1$ is a methyl group.

9. The pyridazinone compound according to claim 1, wherein R$^2$ is hydrogen or a C$_{1-3}$ alkyl group.

10. The pyridazinone compound according to claim 1, wherein R$^2$ is hydrogen or a methyl group.

11. The pyridazinone compound according to claim 1, wherein R$^3$ is hydrogen.

12. The pyridazinone compound according to claim 1, wherein W is halogen, a C$_{1-3}$ alkyloxy group, a (C$_{6-10}$ aryl)C$_{1-3}$ alkyloxy group, a C$_{1-3}$ alkylthio group, a C$_{1-3}$ alkylsulfinyl group, a C$_{1-3}$ alkylsulfonyl group or an N—(C$_{6-10}$ aryl)-N—(C$_{1-3}$ alkyloxycarbonyl)amino group.

13. The pyridazinone compound according to claim 1, wherein W is a C$_{1-3}$ alkyloxy group or a C$_{1-3}$ alkylthio group.

14. A herbicidal composition comprising the pyridazinone compound according to claim 1 and an inert carrier.

15. A method of controlling weeds, which comprises applying an effective amount of the pyridazinone compound according to claim 1 to the weeds or to soil where the weeds grow, wherein the weeds are *Lolium multiflorum, Echinochloa crus•galli* or *Galium aparine*.

16. A method of controlling arthropods, which comprises applying an effective amount of the pyridazinone compound according to claim 1 to arthropods or to habitats of arthropods, wherein the arthropods are *Adoxophyes orana,*

*Spodoptera litura, Culex pipiens pallens, Plutella xylostella, Nilaparvata lugens, Aphis gossypii, Bemisia tabaci* or *Frankliniella occidentalis*.

\* \* \* \* \*